United States Patent [19]
Fritsch et al.

[11] Patent Number: 5,268,266
[45] Date of Patent: Dec. 7, 1993

[54] PROCESS AND NUCLEIC ACID CONSTRUCT FOR PRODUCING REAGENT COMPLEXES USEFUL IN DETERMINING TARGET NUCLEOTIDE SEQUENCES

[75] Inventors: Edward F. Fritsch, Concord; Mary Collins, Natick, both of Mass.

[73] Assignee: Genetics Institute, Inc., Cambridge, Mass.

[21] Appl. No.: 938,201

[22] PCT Filed: Apr. 11, 1986

[86] PCT No.: PCT/US86/00742

§ 371 Date: Jun. 9, 1986

§ 102(e) Date: Jun. 9, 1986

[87] PCT Pub. No.: WO86/06412

PCT Pub. Date: Nov. 6, 1986

Related U.S. Application Data

[63] Continuation-in-part of Ser. No. 729,504, May 2, 1985, abandoned, Ser. No. 607,885, May 7, 1984, Pat. No. 4,766,064, Ser. No. 684,308, Dec. 20, 1984, abandoned, and Ser. No. 684,305, Dec. 20, 1984, Pat. No. 4,766,062, said Ser. No. 684,308, and Ser. No. 684,305, each is a continuation-in-part of Ser. No. 607,885, May 7, 1984.

[51] Int. Cl.$^5$ ............ C12Q 1/68; C07H 21/00; C07H 21/04
[52] U.S. Cl. .................... 435/6; 536/25.3; 536/24.31; 536/24.32; 935/78
[58] Field of Search ........................... 435/6

[56] References Cited

U.S. PATENT DOCUMENTS 4,358,535 11/1982 Falkow .................. 435/6
4,766,062 8/1988 Diamond et al. .......... 435/6

OTHER PUBLICATIONS

Hu et al. Gene 17 (1982) pp. 271-277.
Saiki et al. Science 230 (1985) pp. 1350-1351.
Mullis et al. Cold Spring Harbor Symp on Quant. Biology (1986) pp. 263-273.
Gen Bank Comparison of the Sequence of the 1st Half of M13 Compared to the Second Half of the Phage.
Been et al Methods in Enzymology 101 pp. 90-98 (1983) part C Academic Press New York, N.Y.
Green et al. Nucl Acids Res 1 pp. 1905-1918 (1981).
Berger et al. Methods in Enzymology 152 pp. 401-402 (1987) Academic Press, New York, N.Y.

*Primary Examiner*—Margaret Moskowitz
*Assistant Examiner*—Scott A. Chambers
*Attorney, Agent, or Firm*—Testa, Hurwitz & Thibeault

[57] ABSTRACT

A nucleic acid construct useful in preparing reagents for determining target nucleotide sequences in the nucleic acid of a biological sample, the construct having in its single-stranded form:

(a) a target binding region substantially complementary to the target nucleotide sequence, and (b) a signal strand pairing segment bound in the construct by complementary base pairing to a portion of the target binding region;

a second portion of the target binding region being single-stranded; and the target binding region and signal strand pairing segment being covalently linked by a phosphate/sugar backbone.

A replicable nucleic acid having an origin of replication and two half-restriction sites capable of forming a restriction site can be treated with a restriction enzyme to form a length of nucleic acid containing the target binding region and the signal strand pairing segment. Subsequent labeling of the construct and various optional cleavage and derivation steps can convert the construct to a reagent complex.

12 Claims, 8 Drawing Sheets

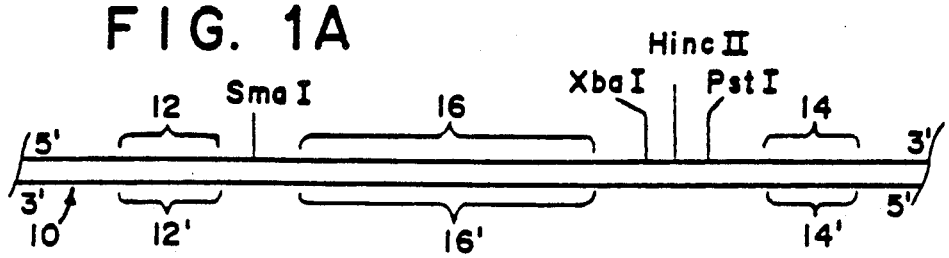
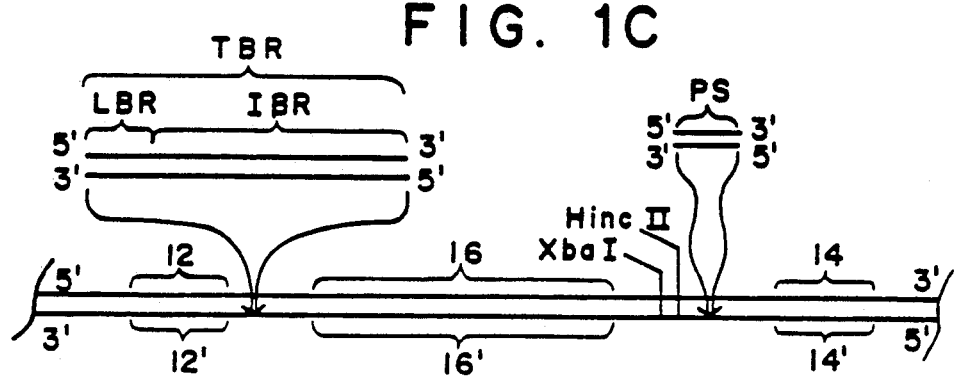
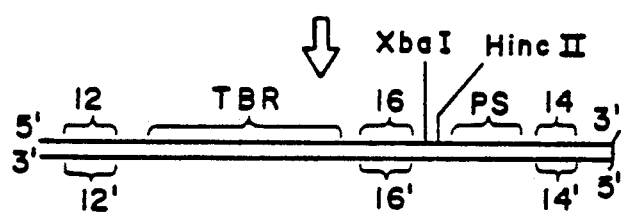
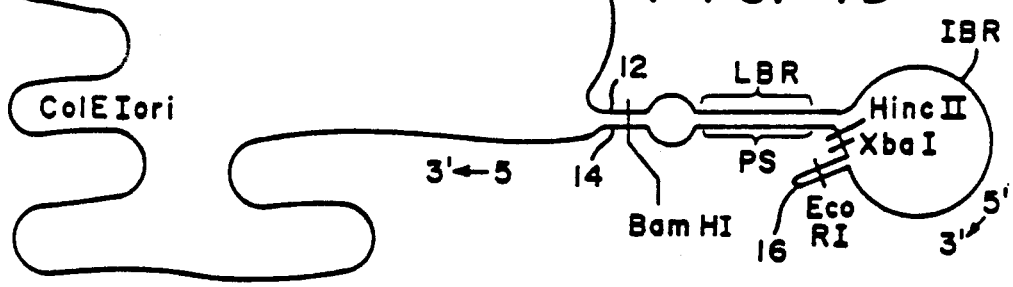
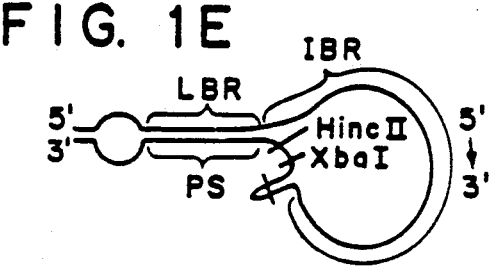
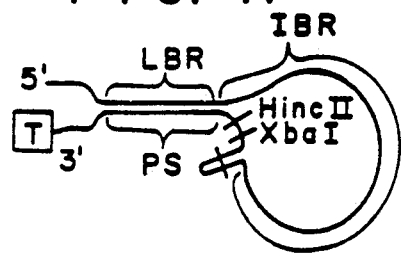

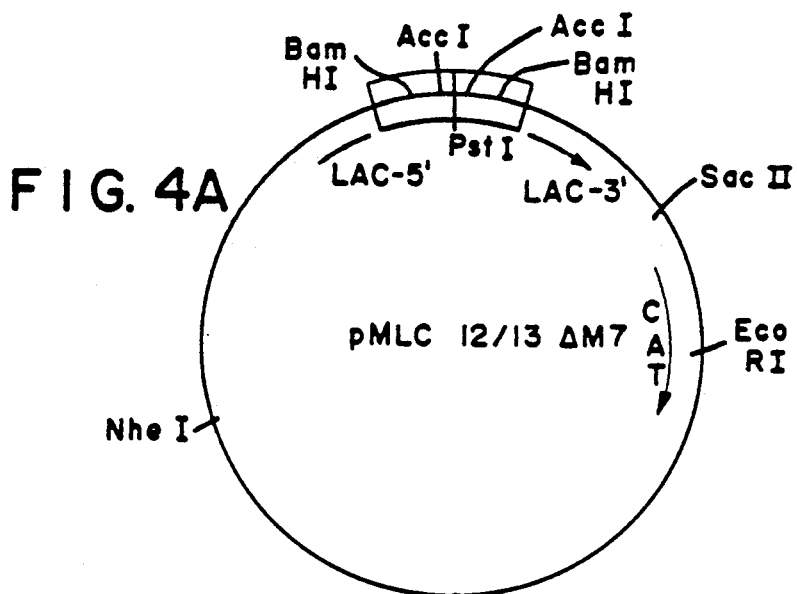
FIG. 4A
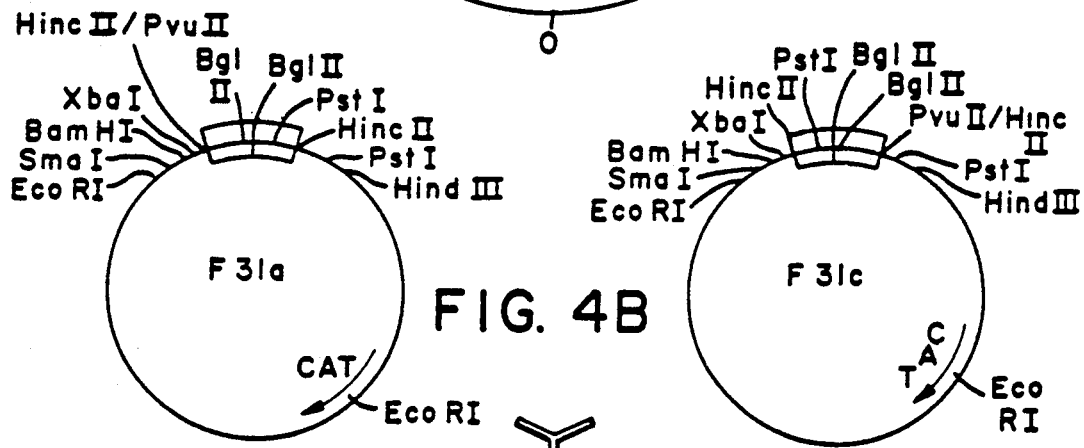
FIG. 4B
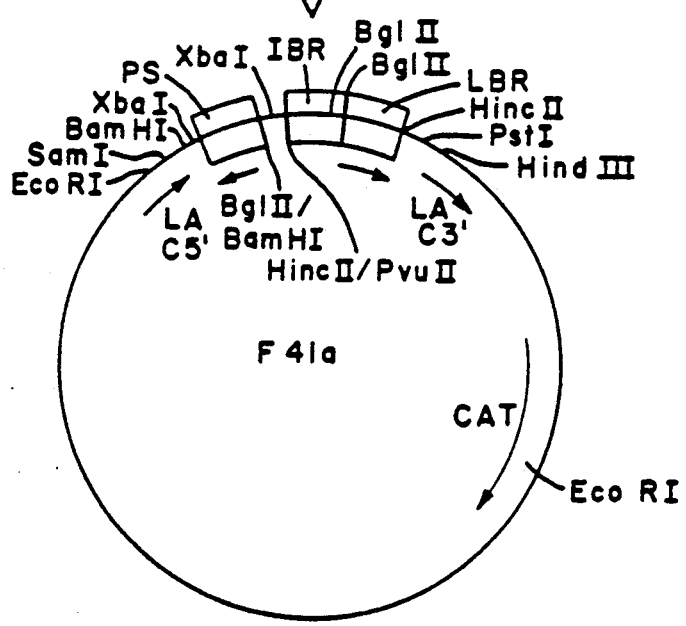

PROCESS AND NUCLEIC ACID CONSTRUCT FOR PRODUCING REAGENT COMPLEXES USEFUL IN DETERMINING TARGET NUCLEOTIDE SEQUENCES

This is a continuation-in-part of U.S. Ser. No. 729,504 of Fritsch et al, filed May 2, 1985, copending and now abandoned, and of U.S. Ser. No. 607,885 of Diamond et al, filed May 7, 1984, copending and now U.S. Pat. No. 4,766,064, U.S. Ser. No. 684,305 of Collins et al, filed Dec. 20, 1984, copending and now abandoned and U.S. Ser. No. 684,308 of Williams et al, filed Dec. 20, 1984, copending and now U.S. Pat. No. 4,766,062. Applications 684,305 and 684,308 were also continuations-in-part of application 607,885.

BACKGROUND OF THE INVENTION

The present invention relates to the production of reagent complexes for the determination of target nucleotide sequences; in particular, novel nucleic acid molecules and constructs are prepared by the process of the present invention which can be replicated and which contain all of the essential nucleic acid components of a reagent complex for a strand displacement assay.

Conventional nucleic acid assays involve a labeled probe polynucleotide. This probe polynucleotide contains a target binding reagent which is complementary to the target nucleotide sequence sought to be assayed. By first immobilizing sample DNA in single stranded form and then probing with the labeled probe polynucleotide, hybridization will occur if and when the target nucleotide sequence is present in the immobilized sample. By washing away unhybridized labeled probe polynucleotide and assaying for label remaining on the surface, a determination can be made whether and how much of the target nucleotide sequence is present in the sample. See U.S. Pat. No. 4,358,535 of Falkow, et al. (1982).

Probe strands complementary to the target nucleotide sequence have been cloned into various vectors for replication before use. Two such types of vectors are viruses having a mature circular single-stranded form (e.g., bacteriophage M13 and bacteriophage F1) and double-stranded circular plasmids (e.g., plasmids pBR322 and PUC) which are replicated in double-stranded form. When such plasmids are provided with origins for replication of a circular single-stranded virus (e.g., the M13 origin of replication), the cells bearing the plasmid having a cloned target binding reagent insert which are infected by the bacteriophage will produce virus particles, some of which contain the plasmid-cloned insert DNA in single-stranded form. See A. Levinson et al., *J. of Mol. & Appl. Genetics*, vol. 2, pp. 507–517 (1984); L. Dente et al., *Nucleic Acids Res.*, vol. 11, pp. 1645-1655 (1983); R. J. Zagursky and M. L. Berman, *Gene*, vol. 27, pp. 183-191 (1984).

Strand migration phenomena have been studied. See, e.g., C. Green and C. Tibbetts, *Nucleic Acids Research*, vol. 9, no. 8, pp. 1905-1918 (1981). The use of strand displacement to assay for the presence and concentration of a target nucleotide sequence is first disclosed in application U.S. Ser. No. 607,885 of S. E. Diamond, et al, "Displacement Polynucleotide Assay Method And Polynucleotide Complex Reagent Therefore" (filed May 7, 1984, copending, and assigned jointly to Allied Corporation and Genetics Institute, Inc.) now U.S. Pat. No. 4,766,064 (see also EPA 164,876, published Dec. 18, 1985, and EPA 167,238, published Jan. 8, 1986). Reagent complexes for such assays require two polynucleotides: (1) a probe polynucleotide containing the target binding reagent complementary to the target nucleotide sequence to be assayed and (2) a labeled polynucleotide (or signal strand) containing a pairing segment complementary to at least a portion of the target binding region of the probe polynucleotide. While each of these polynucleotides may be cloned separately (or one replicated by cloning and the other chemically synthesized), there are significant disadvantages to the necessity of hybridizing the labeled polynucleotide to the probe polynucleotide in the production of reagent complexes for such displacement polynucleotide assays. In particular, one frequently encounters either probe polynucleotide not bearing a hybridized labeled polynucleotide, labeled polynucleotide not bearing a hybridized probe polynucleotide or some of each. While extensive washings and purifications may overcome such incomplete reagent complexes, such treatments are desirably avoided. Furthermore, the other isolation and purification techniques described in application U.S. Ser. No. 729,501, now abandoned, of P. D. Unger, et al., filed May 2, 1985, assigned to Allied Corporation and copending, while substantially reducing the presence of incomplete reagent complexes, nevertheless provide undesired constraints upon the reagent complex and the method for its use.

BRIEF DESCRIPTION OF THE INVENTION

The present invention provides a method and various intermediate structures in the form of nucleic acid constructs which enable the production and replication of novel precursors for reagent complexes useful in nucleic acids strand displacement assays for virtually any target nucleotide sequence. By providing the two polynucleotide portions of the reagent complex in a single replicable structure, and providing a series of easy steps to manufacture operative reagent complexes from the replicable structure, the present invention overcomes the above limitations.

Accordingly, the present invention provides a process of preparing a reagent complex for determining a target nucleotide sequence in the nucleic acid of a biological sample, which process comprises the steps:

(a) producing by replication a continuous nucleic acid molecule predominantly in single-stranded form having:

(i) a target binding region substantially complementary to the target nucleotide sequence, and (ii) a signal strand pairing segment bound in the construct by complementary base pairing to a portion of the target binding region; a second portion of the target binding region being single-stranded, and the target binding region and signal strand pairing segment being covalently linked by a phosphate-sugar backbone;

(b) forming a first terminus adjacent to the signal strand pairing segment and a second terminus adjacent to the target binding region; and (c) attaching a detectable tag.

In many cases, the detectable tag is attached to a terminus adjacent to the signal strand pairing segment and the above three-step process further includes a fourth step:

(d) cleaving the phosphate/sugar backbone covalent linkage of the signal strand pairing segment to the target binding region.

For the four-step process, the forming step (b) (forming the exterior ends) and the cleaving step (d) (forming the interior ends) may be performed in either order or simultaneously. The attaching step (c) normally follows one or both of the forming step (b) and cleaving step (d) and can involve attachment to an interior end, to an exterior end or attachment elsewhere.

The present invention further provides a nucleic acid construct useful in preparing reagent complexes for determining target nucleotide sequences in the nucleic acid of a biological sample, the construct comprising:

(a) a target binding region substantially complementary to the target nucleotide sequence, and (b) a signal strand pairing segment bound in the construct by complementary base pairing to a portion of the target binding region;

a second portion of the target binding region being single-stranded; and the target binding region and signal strand pairing segment being covalently linked by a phosphate/sugar backbone.

The present invention further provides a replicable continuous nucleic acid molecule having:

(a) a target binding region substantially complementary to a target nucleotide sequence which is to be determined, and (b) a signal strand pairing segment complementary to a portion of the target binding region and oriented in the opposite direction to the complementary bases of the target binding region; whereby the continuous nucleic acid molecule, when isolated from its complementary nucleic acid molecule, can form a double-stranded segment with the signal strand pairing segment bound to a portion of the target binding region by complementary base pairing.

It will be appreciated that the replicable nucleic acid molecule described above may be in single- or double-stranded form (i.e., with or isolated from its complementary strand) and may still contain one or more origins of replication. Preferably, the replicable nucleic acid molecule is replicated in a double-stranded form (e.g., a plasmid) bearing origins of replication both for replication in the double-stranded mode by the host cell and replication to form unique single-stranded structures when the host cell is infected with an appropriate virus whose mature form contains single-stranded nucleic acid. Subsequent treatment of the single-stranded form of the replicable continuous nucleic acid molecule of the present invention (see, e.g., FIG. 1D) produces a form of the nucleic acid construct of the present invention (see, e.g., FIG. 1E).

DETAILED DESCRIPTION OF THE INVENTION

Figure 1B:
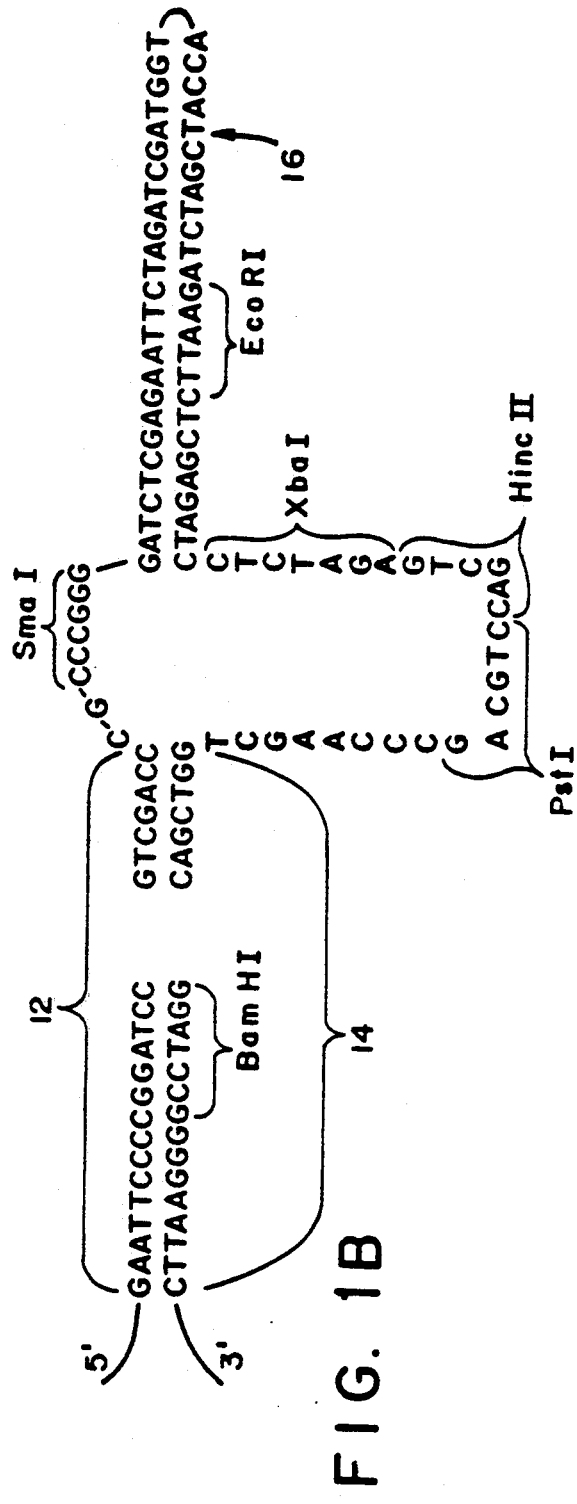

In this application the following terms are used based on their generally accepted meanings in the field of molecular biology:

Polynucleotide or Polynucleotide Strand refers to a linear polymeric structure of pentose sugars (generally ribose or deoxyribose) linked to each other by 3', 5'- phosphodiester linkages, and linked by carbon-nitrogen bonds at the 1-carbon of the sugar to pendant purine or pyrimidine bases such as, but not limited to, uracil (linked naturally to ribose only as rU), thymine (linked naturally to deoxyribose only as dT), cytosine (dC or rC), adenine (dA or rA) and guanine (dG or rG). Polynucleotides thus include strands of deoxyribonucleic acid (DNA) and strands of ribonucleic acid (RNA) or continuous heteropolymers of both types of polynucleotides.

The ends of such Polynucleotide Strands are referred to as the Five Prime (5') ends, where the 5-carbon of the pentose is not linked to another pentose (but may bear hydroxyl, monophosphate or other natural or synthetic moieties), or the Three Prime (3') ends, where the 3-carbon of the pentose is not linked to another pentose (but may similarly bear hydroxyl, monophosphate or other natural or synthetic moieties).

Complementary Base Pairing or Purine/Pyrimidine Base Pairing refers to the hydrogen bonding between opposite bases pendant on two antiparallel Polynucleotide Strands, which is most energetically favorable for natural DNA when dG is opposite dC and dA is opposite dT. Bases other than the five naturally-prevalent ones also have preferential pairing: for example, 5-methylcytosine binds preferentially to guanine. For illustrative purposes, this pairing is shown in many of the Figures by parallel straight lines with apposite strands directed in antiparallel directions (in the 5' to 3' sense). It should be appreciated, however, that the actual geometry of double-standard segment will normally be helical (the well-known double helix) of various pitches, as schematically illustrated in FIG. 1D of U.S. Pat. No. 4,766,062.

Hybridization is used herein to refer to admixing two Polynucleotides under these conditions conducive to the formation of double-stranded structures, with Complementary Base Pairing causing such double stranded structures to form where complementary sequences or nearly complementary sequences are present.

The present invention will be described, first, in terms of the process of the invention. Thereafter, the continuous nucleic acid molecule of the invention, which is present in early steps of the process, will be described further. Next, the nucleic acid construct, which is present in later steps of the process, will be described further. Finally, the reagent complexes (which may be made by the process) and their use will be described. It should be understood that such reagent complexes and methods for their use are, in general, parts of related inventions such as that of U.S. Ser. No. 607,885, filed May 7, 1984, now U.S. Pat. No. 4,766,064 in which the present applicants are co-inventors (see EPA 164,876 and 167,238). Certain forms of the use will be described by reference to various related inventions assigned to Genetics Institute, Inc., to Allied Corporation or to the two companies jointly.

The present invention is also useful in preparing inverse reagent complexes, as described in U.S. Ser. No. 809,992 of Collins and Dougherty, filed Dec. 16, 1985, copending, commonly assigned and now U.S. Pat. No. 4,752,566. In such inverse reagent complexes, the label is attached to or incorporated into the construct near the target binding region (in the sense of staying with the target binding region during manufacture and hybridization with the sample). If such inverse reagent complexes are immobilized, the point of attachment is generally near or in the pairing segment so that the labeled target binding region can be easily separated from the immobilized pairing segment when displacement has occurred. The disclosure of U.S. Ser. No. 809,992 is incorporated herein by reference for a further discussion of inverse displacement. Present Examples 13 and 18 (corresponding to Examples 1 and 2 of U.S. Pat. No. 4,752,566 and to Examples 9 and 10 of U.S. Ser. No. 809,971 now abandoned) illustrate the use of embodiments of the present invention to prepare inverse reagent complexes.

The starting material for the process of the present invention is a replicable continuous nucleic acid molecule. It may be in the form of a nucleic acid strand of a virus (e.g., a bacteriophage), of a plasmid or of other vectors, or of a replicating organism (e.g., a bacterium or yeast). Preferably, the replicable nucleic acid molecule or strand is of a bacteriophage or plasmid and contains one or more origins of replication recognizable by the replication system either naturally present in, or induced by an infecting virus to be in, the host cell. The replicable continuous nucleic acid molecule is normally DNA; forms of the invention wherein the construct may be RNA are described separately below.

The two essential portions of the replicable continuous nucleic acid molecule are a target binding region and a signal strand pairing segment. These two nucleic acid sequences are the precursors for corresponding segments of the reagent complex used in the method of U.S. Pat. No. 4,766,062 to determine or detect a target nucleotide sequence in a biological sample. Accordingly, for reasons discussed in U.S. Pat. No. 4,766,062, the overall target binding (TBR) may be of any desired length to impart sufficient specificity, but is commonly about 35 to about 2000 nucleotides in length, and is preferably about 100 to about 1000 nucleotides in length. The manufacturing process of the present invention imposes no substantial limitations upon the choice or size of target binding region.

The signal strand pairing segment (PS) is the precursor for the portion of the labeled polynucleotide (L in U.S. Pat. No. 4,766,062), called herein the signal strand, that is bound by complementary base pairing to a portion (LBR) of TBR in the reagent complex. As indicated in U.S. Pat. No. 4,766,062 the length of LBR can be, for example, 20 to 1000 nucleotides, and is preferably 50 to 500 nucleotides and is more preferably 100 to 300 nucleotides. It will be appreciated that a target binding region larger than LBR leaves one or more initial binding regions (IBR) as discussed in U.S. Pat. No. 4,766,062. The pairing segment (PS) has a corresponding length to LBR, but contains the complementary bases (except for any permissable mismatches) and is in inverse order within the replicable nucleic acid molecule. As described in more detail below, the inverse order of complementary bases in PS compared to LBR (part of TBR) permits the continuous nucleic acid molecule, once in single-stranded form (isolated from its complementary strand) to form a double-stranded region with PS bound to LBR. As indicated in U.S. Pat. No. 4,766,062, some mismatched bases may exist in the region of complementary. As illustrated by FIG. 1D (and described later), there may be other regions of local double-strandedness besides LBR-PS, and the replicable nucleic acid molecule may still be intact. While this inverted repeat structure is normally able to form upon isolation from the complementary strand, it is contemplated that such formation may, in some cases, be aided by linearization of the nucleic acid molecule or by other biochemical, chemical or physicochemical steps such as selected conditions of temperature or ionic strength.

In certain preferred forms of the continuous nucleic acid molecule, a restriction site recognizable by and cleavable by a restriction endonuclease, is also formed in the continuous nucleic acid molecule isolated from its complementary strand (see the Bam HI site in FIG. 1D). Cleaving that site cuts the continuous nucleic acid molecule at two points. By locating those two points on the exterior of a segment including and connecting TBR and PS covalently (by the phosphate sugar backbone), a length of nucleic acid can be isolated from the remainder of the replicable nucleic acid molecule. Alternatively, the two points can be restriction sites created by separate inverted repeats (as is segment 16 in the Figures). This length either has the LBR/PS double-stranded segment or can form such segment. There is no critical maximum on the nucleotides not part of TBR or of PS. This length of nucleic acid, containing both TBR and PS, and having PS bound by base pairing to a portion (LBR) of TBR is called herein the nucleic acid construct.

As discussed below, the nucleic acid construct may be RNA transcribed from a DNA nucleic acid molecule, either directly or after cutting a long DNA molecule which contains an origin of transcription.

As formed, the nucleic acid construct has two ends (a 5 Prime End and a 3 Prime End), one of which is exterior of TBR along the nucleic acid chain, the other of which is exterior of PS along the nucleic acid chain. As described more fully below, each of these two ends may be used in preparing reagent complexes or, alternatively, one of these ends and one new end created by cutting between TBR and PS may be used. While the additional cut will create two new ends (a second 5' Prime End and a second 3' Prime End), normally, at least one of the initially-created (exterior) ends is used.

While much of the present description is of a process wherein the exterior ends are created first (to produce the nucleic acid construct) and then the interior cut (if any) is made, such order may be reversed or the two sets of cuts may be made concurrently or without any intervening purification or separation. Furthermore, as discussed at the end of Example 7, the continuous nucleic acid molecule can be labeled and used in a displacement/capture assay without creating either exterior or interior ends.

At some point, for the preparation of ordinary reagent complexes to be used in the method of U.S. Pat. No. 4,766,062, a detectable tag is attached to an end adjacent to the signal strand pairing segment. For inverse reagent complexes (see U.S. Pat. No. 4,752,566 ), the tag is normally attached to an end adjacent to the target binding region. The term "adjacent to" in this context means sufficiently close, as measured topologically along the polynucleotide chain (as distinct from spatially) that the tag will remain with the signal strand pairing segment (or, for inverse reagent complexes, with the target binding region) throughout the process of preparing reagent complexes, and will remain with the signal strand (or, for inverse reaent complexes with the target binding region) if it is displaced from TBR (or from PS) by a target nucleotide sequence. The end to which the detectable tag is attached may be an interior end or an exterior end, and may be a 5 Prime end or a 3 Prime end. As described below and in U.S. Pat. No. 4,752,566, if the entire ordinary or inverse reagent complex is to be captured after displacement, there are suitable forms of the invention wherein the tag is attached randomly at one or more sites on the molecule, e.g., by photochemical or non-specific chemical reaction (see Example 9).

Suitable detectable tags include those described in U.S. Pat. No. 4,766,062, including radioisotopes, fluorescent molecules, enzymes and chemiluminescent tags.

Other suitable detectable tags are lengths of ribonucleotides and especially of poly (riboadenosine) as described in C. Vary, et al., U.S. Pat. No. 4,767,699, filed May 2, 1985, assigned to Allied Corporation, copending and now U.S. Pat. No. 4,767,699. At the 3 Prime End, various such tags can be incorporated by chain elongation, especially with terminal deoxynucleotidyl transferase (TdT). Elongation with ribonucleotides and especially riboadenosine may involve the enzyme polynucleotide phosphorylase (PNP), as described in that application.

Detectable tags may also be attached by chemical modification, by ligation using splint oligonucleotide or by a combination of ligation and chemical modification as described in E. Brown, et al., U.S. Ser. No. 729,700 now abandoned, filed May 2, 1985, commonly-assigned, and copending. Such techniques may be specific for any 5 Prime end, for any 3 Prime end or (especially when ligation is involved) for 5 Prime or 3 Prime ends having specified sequences.

In some forms of the invention applied to the reagent complexes of U.S. Pat. No. 4,766,062, an end (interior or exterior) adjacent to the target binding region (TBR) is also used. Normally, such end is either attached to a solid phase to create an immobilized probe polynucleotide (as described in U.S. Pat. No. 4,766,062), or is attached to a moiety (e.g., biotin), that can be selectively attached to a solid support at a later time (normally after the assay method). Such use of an immobilizable probe is described in U.S. Pat. No. 4,766,062. Additional forms of such immobilizable probe are described in Unger, et al., U.S. Ser. No. 729,501 now abandoned, copending, assigned to Allied Corporation and filed May 2, 1985. In similar fashion, for preparing certain forms of the inverse reagent complexes of U.S. Pat. No. 4,752,566, an end (interior or exterior) adjacent to the pairing segment (PS) can be either attached to a solid phase (immobilized) or rendered immobilizable. Techniques for rendering such end immobilizable include elongation with biotinylated dUTP, elongation with dCTP (to form poly-dC) or attachment chemically of biotin or some other affinity moiety.

The reagent complexes made in accordance with the present invention can be used for the detection and determination of a variety of target nucleotide sequences in a variety of concentrations. In particular, microorganisms including infectious agents whose nucleic acid (genomic or otherwise) could be targeted include pathogenic viruses, bacteria and fungi; e.g., cytomegalovirus or Neisseria gonorrhea. Exemplary genetic disorders or conditions which could be targeted include $\beta$ thalassemias, $\alpha_1$-thalassemias, cri du chat syndrome and some retinoblastomas. The methods and reagents of U.S. Pat. No. 4,766,062 are applicable to detecting genetic disorders or variations primarily when a multibase nucleotide deletion, insertion, substitution or transposition is involved in distinguishing the target sequence. To the extent that such methods are applicable to genetic disorders due to single base mutations, if at all, the complement of the substituted base or other point of mutation is desirably part of the target binding region of the probe polynucleotide, with the location of that base within the region likely to affect the selectivity of the method. Among changes in structural or regulatory genes, changes or differences in the expression, activation or rearrangement of oncogenes can be detected by the present process. Other perturbations in the expression of structural genes can be similarly detected. Such reagent complexes can also be applied to HLA typing for tissue transplantation, determination of antibiotic resistance genes in microorganisms, and to the screening of food, medicinal and water samples for specific infectious agents or other microorganisms.

Selecting a target sequence for a particular test may involve determining a sequence which is unique or relatively unique to the target organism or condition. Such target sequences would be used to develop the target binding region as complementary thereto, and then a pairing segment for the signal strand polynucleotide of appropriate length would be developed to bind to a part of the target binding region. Such segments can then be inserted into a cloning vector as described below.

FIG. 1A illustrates one embodiment of a double-stranded nucleic acid 10, the top strand of which forms a part of the replicable nucleic acid molecule of the present invention. The top strand of segment 10 has, from left to right (being the 5' to 3' direction), a first segment 12, an intervening region with an Sma I restriction site, a second segment 16, an intervening region with an Xba I restriction site, an Hinc II restriction site and a Pst I restriction site and a third segment 14 at the 3' end of the top strand of nucleic acid 10. The bottom strand, in antiparallel direction, is fully complementary and has from right to left (its 5' to 3' direction): a segment 14' of the bottom strand complementary to the third segment 14, an intervening region, a segment 16' of the bottom strand complementary to second segment 16, an intervening ion and a segment 12' of the bottom strand complementary to first segment 12. The intervening regions, being fully complementary, complete, respectively, the Sma I restriction site between the 12/12' region and the 16/16' region and the Xba I, Hinc II and Pst I restriction sites between the segment 16/16' region and the 14/14' region.

Nucleic acid 10 may be part of any of a variety of double-stranded nucleic acids, including genomic DNA of a microorganism of various cells, and including plasmids, viruses and other vectors capable of replication in double-stranded form in a host cell.

FIG. 1B illustrate the top strand of nucleic acid 10 shown in FIG. 1A in continuous (primarily single-stranded) form. As explained in the discussion above, the single-stranded form may be produced by physicochemical manipulation or may represent the native form of a virus such as M13 (which is in double-stranded form during replication). Preferably, the single-stranded form is the result of incorporation of one strand of a normally double-stranded polynucleotide into virus particles (e.g., by M13 infection of a microorganism containing a double-stranded plasmid DNA having an M13 origin of replication).

In FIG. 1B, the precise sequence of the single (top) strand is shown, with various restriction sites and half-restriction sites also shown. The term "restriction site" is meant to indicate a double-stranded region having a sequence recognizable by and cleavable by a specific restriction endonuclease. The term half-restriction site is meant to indicate a single-stranded nucleotide segment which, when it is hybridized to the perfectly matched nucleotide segment, forms such a restriction site. Because segments 12 and 14 of this top strand from FIG. 1A are complementary to each other, they form a 22 base pair duplex segment having a Bam HI restriction site at bases 10–15 of segment 12 (counting from the 5' end of segment 12) and at the corresponding bases of segment 14. Segment 16 is self-complementary, such that this 52 nucleotide segment forms a 26 base pair duplex hairpin structure, with an Eco RI restriction site at bases 9–14 and 39–44 of segment 16. The first intervening sequence (with an Sma I half-restriction site) and the second intervening sequence (with Xba I, Hinc II and Pst I half restriction sites) each join the segment 12/14 duplex to the segment 16 duplex hairpin structure with short single-stranded nucleotide sequences.

In FIG. 1C insertion of two double-stranded nucleotides into nucleic acid 10 is shown. At the Sma I site (see FIG. 1A) a double-stranded polynucleotide TBR is inserted having a left portion (LBR) and a right portion (IBR). As indicated below, the combination of LBR and IBR will be chosen such that a defined segment (TBR) of one strand is complementary to a target nucleotide sequence that is desired to be determined or detected. The TBR insert is shown here as having LBR on the exterior (left) side and IBR in the interior (right) side. At the Pst I site (see FIG. 1A) a segment PS is inserted that is substantially homologous (in an inverse orientation) to the LBR portion of the first insert TBR.

The generality of the present invention can be appreciated by considering that any sequence of virtually any length can be synthesized, cloned or otherwise obtained and inserted in the desired orientation as the first insert (at the Sma I site) for use as the target binding region TBR of the probe polynucleotide. Thereafter, any convenient portion of the first insert can be chosen and its complementary sequence either chemically synthesized, replicated or both to serve as the second insert PS (which will ultimately serve as the pairing segment of the signal strand or labeled polynucleotide).

FIG. 1D shows a complete circular single-stranded DNA molecule (the replicable nucleic acid molecule of the invention in single-stranded form) containing the top strand from the product of insertion as illustrated in FIG. 1C. It has been isolated from its complementary strand (which contains segments 10', 12', 14' and 16'). Looking in the direction from the 5' end to the 3' end of each segment, the main loop of the circular DNA is connected by segment 12 and a short single-stranded segment to segment LBR, then segment IBR, then the hairpin 16, then a single-stranded segment containing half restriction sites Xba I and Hinc II, then segment PS (hybridized to segment LBR), then a short single-stranded sequence, then segment 14 (hybridized to segment 12) and finally back to the other (5') end of the main loop. The main loop contains a segment CE which, when it is in double-stranded form, could serve as an origin for replication in double-stranded form (col EI origin in the embodiment of the Examples). The main loop also has an origin for M13 replication (shown as M13 ori).

Cleavage of the circular, primarily single-stranded DNA shown in FIG. 1D by the restriction endonuclease Bam HI (at a Bam HI site within segment 12/14, see FIG. 1B) produces the loop shown in FIG. 1E with only short pieces of DNA to the left of the segment LBR/segment PS duplex. Depending upon temperature and salt concentration, these pieces may be single-stranded or joined at the end by a 12 based-paired duplex. In particular, the 5' end structure is 5'-GATCCGT CGACCCGCCC-LBR; the 3' end structure is 3'-GCAGCTGGTCGAACCCG-PS; and the eight underlined nucleotides can be base-paired. The GATC overhang at the 5'-end is referred to below.

At this point, a second nucleic acid construct has been formed which includes:

(a) a target binding region (segments LBR and IBR) substantially complementary to the target nucleotide sequence, and (b) a signal strand binding region (segment PS) bound in the construct to a portion (LBR) of the target binding region, a second portion (IBR) of the target binding region being single stranded, the target binding region and signla strand binding region being covalently linked by a phosphate/sugar backbone (the segment joining PS to IBR which includes hairpin 16 and half-restriction sites Xba I and Hinc II). Such construct may be separated from the larger DNA fragment, e.g., by hydroxyapatite chromatography.

The nucleic acid construct is now susceptible to a variety of the specific chemical or biochemical modifications at either the existing 3' end, the existing 5' end or at 3' and 5' ends that will be created when the Eco RI restriction site of hairpin 16 is cleaved. A first example of such series of modifications is illustrated in FIGS. 1F and 1G.

Starting with the nucleic acid construct of FIG. 1E, the 3' end (near segment PS) can be modified to attach a detectable tag T as shown in FIG. 1F. Purely chemical-modifications may be used such as described in U.S. Pat. No. 4,766,062. Biochemical modifications that may be made specifically at this 3' end include those based either upon filling in of the bases CTAG complementary to the GATC overhang left in single-stranded form by the action of Bam HI restriction endonuclease (see above sequence of the 5' end), or by elongation at the 3' end by the action of various enzymes such as terminal deoxynucleotidyl transferase.

In such fashion radioactively labeled nucleotides may be added to the 3' end. Nucleotides such as biotinylated uridine may also be added to the 3' end by elongation with deoxynucleotidyl terminal transferase; such elongation may be followed by binding streptavidin-enzyme conjugates to the pendant biotins. Alternatively, a series of riboadenosine nucleotides may be added by the combined action of deoxynucleotidyl terminal transferase followed by polynucleotide phosphorylase as described in application U.S. Ser. No. 729,503 of C. Vary, et al. entitled "Diagnostic Reagent, Kit And Method Employing Polynucleotide Displacement, Separation, Enzymatic Cleavage And Adenosine Phophate Detection," and in U.S. Pat. No. 4,735,897 also filed May 2, 1985.

Figure 1G:
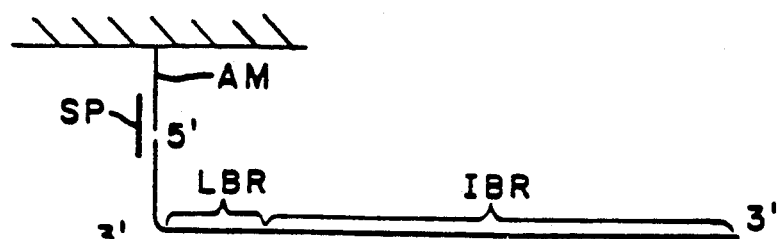

Whichever tag is chosen, the tagged construct of FIG. 1F may now be attached to a solid phase specifically by the free 5' end as illustrated in FIG. 1G. Looking at the top portion of the FIG. 1G, a DNA attachment moiety AM is covalently attached to a solid phase and a splint oligonucleotide (SP) is used to hybridize both to the 5' end of the tagged second construct and the 3' end of the attachment moiety AM. Ligation forms a complete covalent attachment of the tagged construct to the solid phase. The steps for this attachment may be presented in several orders, with one preferred order being to: (1) hybridize attachment moiety, splint and nucleic acid construct, (2) ligate to form a covalent link between the attachment moiety and the free 5' end of the construct adjacent to TBR, and (3) chemical attachment of the other end of the attachment moiety to the support. See E. Brown et al., U.S. Ser. No. 729,700 now abandoned. By then digesting with restriction endonuclease Eco RI, the construct can be cut at the hairpin 16, causing the probe polynucleotide P (containing segments LBR and IBR) to cease to be covalently linked to a labeled polynucleotide L (as in FIG. 1G) This severing may occur before or after attachment to the support. The labeled polynucleotides contain segment PS and the half-restriction sites Hinc II and Xba I, as well as the tag T. The labeled polynucleotide L remains bound to the probe polynucleotide P via the purine/pyrimidine hydrogen bonding between segment PS and segment LBR.

As described more in fully in application U.S. Pat. No. 4,766,062 this reagent complex may now be used to assay for a target nucleotide sequence complementary to segments LBR and IBR. A sample, if it contains the target nucleotide sequence, will hybridize first at the single-stranded portion IBR of the probe polynucleotide P (the right end of probe P in FIG. 1G), forming a duplex structure, and thereafter, branch migration will occur toward the left in FIG. 1G. While the branching point may shift back and forth to the left and right, especially within segment LBR which is complementary both to the pairing segment PS of the labeled polynucleotide L and a portion of the target nucleotide sequence, eventually the branch will shift sufficiently to the left that the labeled polynucleotide L will dissociate from the probe polynucleotide P. Under normal conditions, such displacment of the labeled polynucleotide L can occur quickly after the beginning of hybridization of the target nucleotide sequence to the initial binding region IBR (typically within 30 minutes of total assay time and, on a microscopic level, within seconds of initial hybridization at segment IBR).

By separating the liquid phase containing displaced labeled polynucleotides L from the solid phase containing attached intact reagent complexes, and then assaying for the tag T in either phase (but preferably in the liquid phase), a measurement can be made which is both qualitatively and quantitatively a function of the presence and the concentration of the target nucleotide sequence in the sample. Such method of use is described in greater detail in U.S. Pat. No. 4,766,062.

Figure 1H:
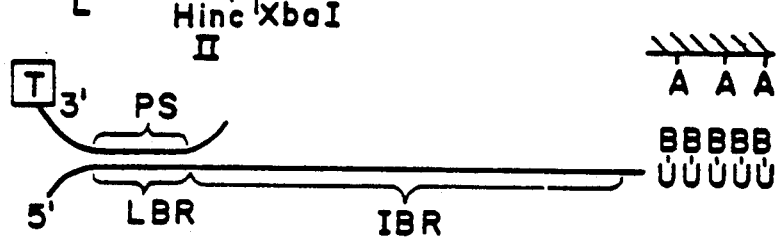

FIG. 1H shows an immobilizable reagent complex that can be prepared from the tagged construct of FIG. 1F. By digesting the tagged construct of FIG. 1F with restriction endonuclease Eco RI, the hairpin 16 is cleaved, removing the covalent attachment of the probe polynucleotide to the labeled polynucleotide L. A second 3' end is now created near the 3' end of segment IBR. Assuming that the tag T is one which blocks chain elongation, the action of terminal deoxynucleotidyl transferase in the presence of biotinylated uridine (see EPA 63,879 (1982)) will attach a series of uridine nucleotides with pendant biotins as shown on modified probe P' in FIG. 1H. Such pendant biotins may now serve as a site for attachment by immobilized avidin or streptavidin (shown as A's on a solid phase). As indicated in U.S. Pat. No. 4,766,062 such affinity attachment may either serve as part of the preparation of an immobilized reagent complex or serve as a means of separation following a specific displacement assay run in solution.

Figure 3B:
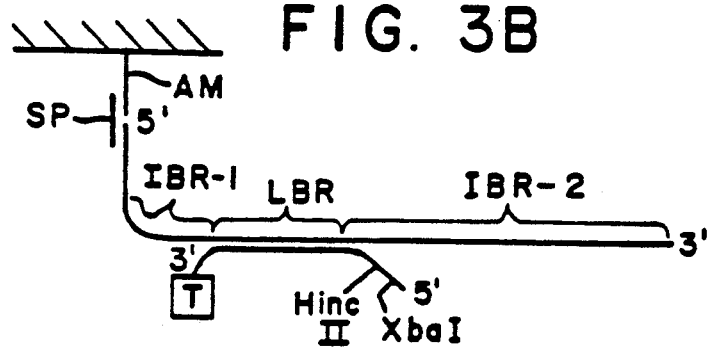

In many forms of the invention, two internal half-restriction sites between segment TBR and segment PS within the construct can pair to form a restriction site (hairpin 16 having an Eco RI site in FIGS. 1D and 1E) which is cut at some point in the process. Other forms of recognizable cleavage sites could be used in place of such hairpin. There are many other forms of the invention, however, in which such a site need not be present or, if present, that it need not be cut during the process, provided that some means is present for distinguishing: (1) segments PS bound by complementary base pairing to segments LBR from (2) segments PS unbound by complementary base pairing (displaced from) segment LBR. As indicated in FIG. 3C of U.S. Pat. No. 4,766,062 and the accompanying description, a second tag may be present on the probe polynucleotide which is in spatial proximity to the tag on the labeled polynucleotide when PS is bound to LBR. Upon displacement of PS from LBR, the two tags become separated spatially, even though still attached by the nucleotide chain. If, for example, one tag is a fluorescer and the other tag is a quencher, then the fluorescent signal can be detected selectively from constructs which have been subjected to displacement by target nucleotide strand. Referring to present FIG. 1E, such a construct can be formed by attaching the fluorescer to the (exterior) 3' end adjacent to LBR and by attaching the quencher to the (exterior) 5' end adjacent to PS.

Figure 2B:
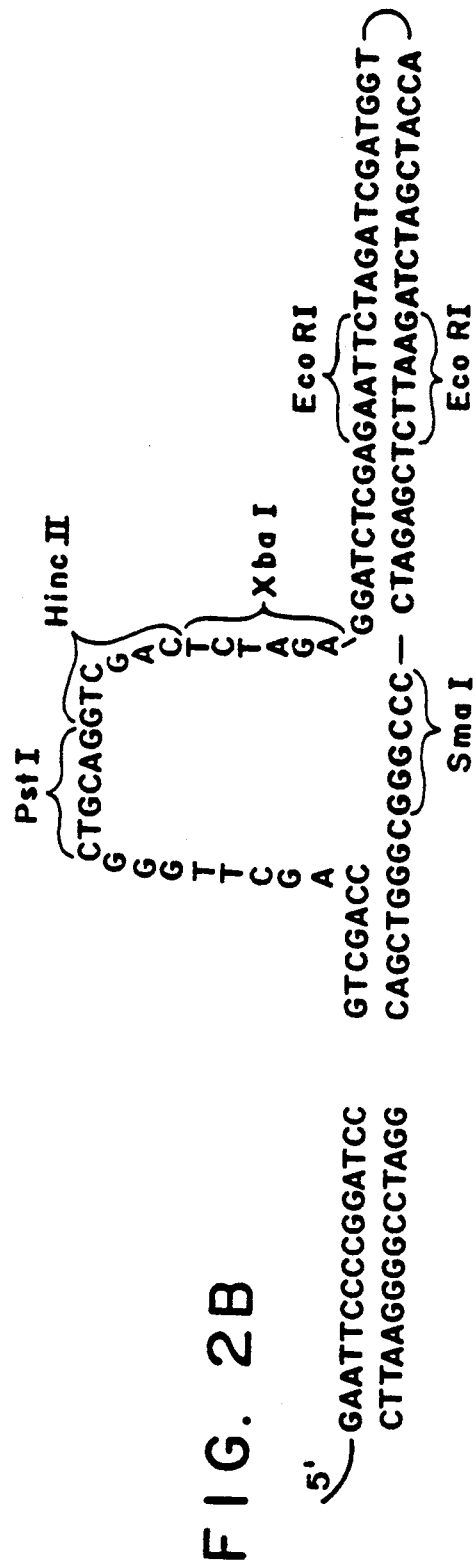
Figure 2A:
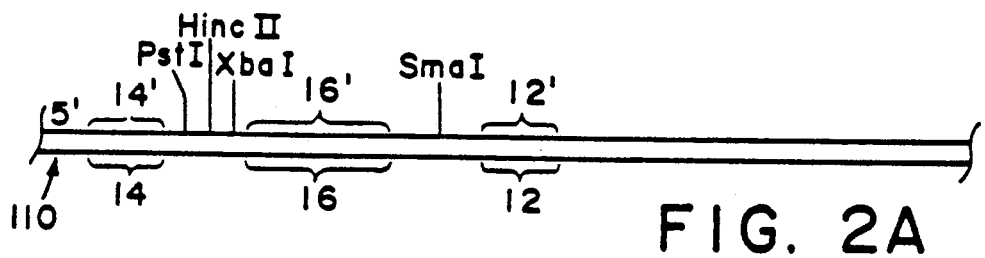

FIG. 2A illustrates a nucleic acid precursor 110 of double stranded nucleic acid. The region of DNA shown in FIG. 2A comprises a sequence having segments 12, 16 and 14 and the half-restriction sites Sma I, Xba I, Hinc II and Pst I, which have been placed in nucleic acid 110 in a vector (which includes the M13 and plasmid origins of replication and a selectable marker) in an orientation opposite to that of FIG. 1A.

Thus, in FIG. 2A, the top strand contains from left to right (the 5' to 3' direction): segment 14', the Pst I, Hinc II and Xba I half-restriction sites, segment 16', the Sma I half-restriction site and segment 12'. FIG. 2B illustrates the top strand of nucleic acid precursor 110 shown in FIG. 2A in continuous (primarily single-stranded) form, and thus corresponds to the view of FIG. 1B.

FIG. 2B shows that insertion of the segment in the opposite orientation places segments 14', 16' and 12' in the top strand, which is the strand found in mature virus particles. Therefore, the Sma I site is now near the 3' end that will be created when segment 12' is cleaved; and the Pst I site is now near the 5' end that will be created when segment 14' is cleaved.

Figure 2C:
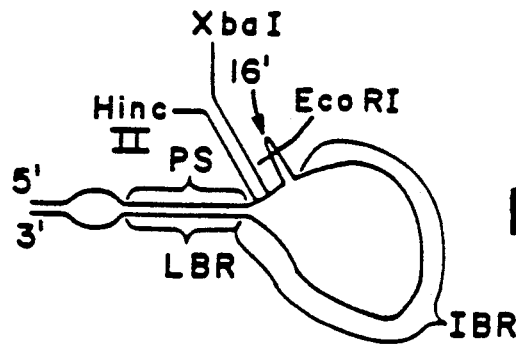

FIG. 2C illustrates a second embodiment of the nucleic acid construct of the present invention that can be prepared from the precursor shown in FIGS. 2A and 2B. FIG. 2C is analogous to FIG. 1E in that the TBR segment (including LBR and IBR) has been inserted at the Sma I site and the PS segment inserted at the Pst I site and the resulting circular single-stranded DNA has been cleaved with restriction endonuclease Bam HI. This construct now contains a free 3' end adjacent segment LBR and contains a free 5' end adjacent segment PS. Attachment of the tag specifically at the 5' end can proceed via a variety of techniques: as described below polynucleotide kinase can replace the terminal 5' phosphate with a P-32 labeled phosphate. Furthermore, chemical attachment schemes can be used to attach a variety of detectable tags including fluorescent, enzymatic and chemilumiscent tags specifically to the 5' end. Furthermore, ligation or a combination of ligation and chemical attachment may be used, as described in U.S. Ser. No. 729,700 now abandoned, of E. Brown, et al, referenced above.

Once the tagged (at the 5' end) nucleic acid construct is formed, it may then be digested with the restriction endonuclease Eco RI. This enzyme cleaves the hairpin 16, forming the linear structure shown on the left side of FIG. 2D. In this linear structure, the labeled polynucleotide L contains the pairing segment PS and at its 5' end the detectable tag T. The longer polynucleotide, probe polynucleotide P, contains segments LBR and IBR. While the polynucleotides L and P are no longer covalently joined, they are joined by hydrogen bonding between segments PS and LBR. Furthermore, while both polynucleotide L and P have free 3' ends, only the probe polynucleotide P has a free 5' end.

Figure 2D:
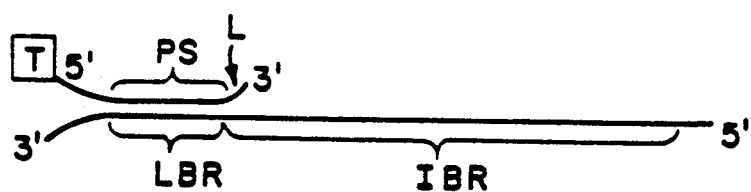

Referring to the remainder of FIG. 2D, the 5' end of the probe polynucleotide P of the reagent complex may now be attached to a solid surface SU by an attachment moiety AM and a splint SP (followed by ligation) as described in more detail in application U.S. Ser. No. 729,700 of E. Brown, et al. now abandoned. Thereafter, the immobilized reagent complex may be used for a displacement assay as described in U.S. application Ser. No. 607,887 of S. E. Diamond, et al (U.S. Pat. No. 4,766,064). Alternatively, rather than attaching the 5' end of the probe polynucleotide P of the reagent complex of FIG. 2C to a support, a moiety B may be attached at the 5' end of the probe polynucleotide P (such as biotin or iminobiotin via ligation to a second attachment moiety containing biotin or iminobiotin) so that the displacement reaction may be run in solution. After completion of displacement reaction, the attached moiety at the 5' end of the probe P can be used to trap with an immobilized affinity reagent (e.g., streptavidin) all of the intact reagent complexes. Under these circumstances, only displaced labeled polynucleotides L (no longer bound to probe polynucleotide P) should pass through the immobilized affinity material for detection. Again, the quantity of tag detected in the eluant from a column of immobilized affinity reagent will be functionally related to the presence and concentration of target nucleotides sequence present in the sample used for the displacement.

It should be appreciated that a replicable nucleic acid molecule and embodiments of the nucleic acid construct having similar 5' ends adjacent to PS and similar 3' ends adjacent to TBR can also be produced by reversing the insertion shown in FIG. 1C into the precursor strand 10 shown in FIG. 1A. One would thus introduce segment PS at the Sma I site (using appropriate end nucleotides) and introduce segment TBR at the Pst I restriction site (using appropriate end nucleotides). Thus, the specificity of which segment (TBR or PS) is adjacent to a free (exterior) 5' or 3' end can be determined on the basis of which precursor replicable nucleic acid molecule is used (molecule 10 of FIG. 1A or molecule 110 of FIG. 2A) and which sites (Sma I or Pst I) the TBR or PS are inserted at. It should be appreciated that the Sma I and Pst I sites are specified as such for illustrative purposes based upon the precursor nucleic acid molecule of Example 4. One skilled in the art could find other half-restriction sites or other techniques to specifically place or clone segments TBR and PS in the desired location and orientation.

Inverse reagent complexes can similarly be constructed from the constructs either of FIG. 1E or of FIG. 2C, with the attachment of a tag now being directed specifically to the end (the 5' End in FIG. 1E; the 3' End in FIG. 2C) adjacent to the target binding region TBR (IBR plus LBR). If one desires to then immobilize the pairing segment PS or render it immobilizable, appropriate chemical or biochemical modification can then occur at the other exterior end (the 3' End in FIG. 1E; the 5' End in FIG. 2C) or, after cleaving the hairpin, at the interior end formed adjacent to the pairing segment PS.

Figure 3A:
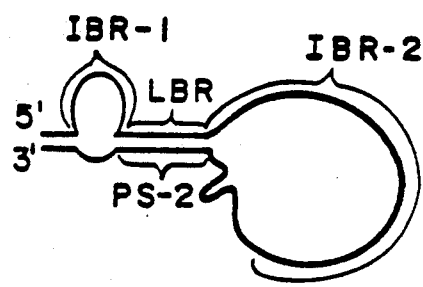
Figure 3C:
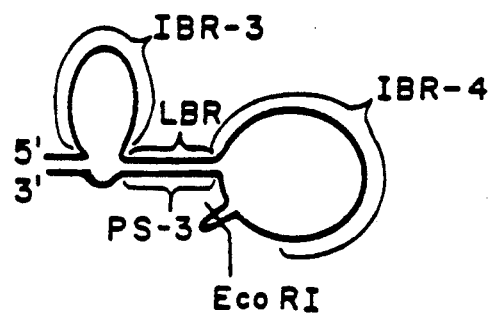
Figure 3D:
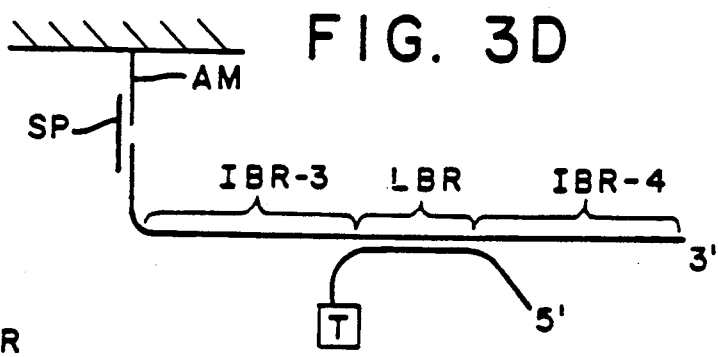
Figure 3E:
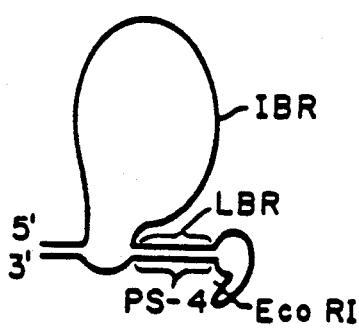

FIGS. 3A, 3C and 3E illustrate three modifications of the nucleic acid construct of FIG. 1E. Each of these modified forms can be produced by methods similar to those shown in FIG. 1C, but using pairing segments PS complementary to different portions of the first insert TBR. Thus, in FIG. 3A, a pairing segment PS has been chosen for insertion at the Pst I site (see FIG. 1A) which is complementary to the second fifth of the target binding region TBR. Under these conditions, the second construct of FIG. 3A contains a significantly longer (compared to the second construct of FIG. 1E) single-stranded portion near the 5' end, which portion now contains the 5' end of the target binding region (IBR-1). Dissociation of the relatively short duplex region at the ends of the nucleotide strand will now create a significantly longer 5' end for elongation analogous to that illustrated in FIG. 1H. Furthermore, the labeled polynucleotide L will now be present nearer to the middle of the target binding region TBR in the immobilized reagent complex, shown in FIG. 3B, that can be produced (compare FIG. 1G).

FIG. 3C illustrates a nucleic acid construct, similar to that shown in FIG. 1E, but now with pairing segment PS complementary to a labeled polynucleotide binding region LBR near the middle of the target binding region TBR. This shift increases the size of the 5' single-stranded region (including IBR-3) of the second construct and decreases the looped portion (including IBR-4) between segment LBR and the hairpin 16. FIG. 3D shows a reagent complex that can be prepared therefrom.

FIG. 3E illustrates a nucleic acid construct similar to that illustrated in FIG. 1E, but now with the pairing segment PS complementary to a segment LBR at the 3' end of the target binding region TBR. Now all of the initial binding region IBR is closer to the 5' end than the labeled binding region LBR. Therefore the hairpin 16 forms the major portion of the loop connecting the duplex PS/LBR. Once a tag is attached to the 3' end and the 5' end is immobilized, (followed by cutting the hairpin Eco RI restriction site), a reagent complex will be created in which the labeled polynucleotide L is hybridized to the distal end of the probe polynucleotide P relative to the solid phase to which the 5' end of the probe polynucleotide is attached.

Referring again to FIGS. 1D and 1E, one can also provide for different lengths of intervening sequences, especially between segment 12 and segment LBR. Additional nucleotides inserted there, either as a part of the precursor nucleic acid or along with LBR and IBR in the insert, will lengthen the spacing in FIG. 1F between the exterior 5' end and segment LBR. Such lengthening would (like the constructs of FIGS. 3A, 3C, and 3E) increase the spacing between a 5' end attachment (e.g., to the support as in FIG. 1G) without splitting IBR or placing any of IBR closer to the 5' end than LBR.

Exemplary constructs formed from RNA may be also made using, for example, the SP6 vectors of D. A. Melton, et al., *Nucleic Acids Res.*, vol. 12, pp. 7035-7056 (1984). These vectors, commercially available from Promega Biotec, are derived from pUC12 and contain an SP6 transcription promoter and a polylinker next to the promoter. Fragments of interest, having segments analogous to TBR and PS, would be cloned into different sites in the polylinker region, in an inverted orientation with respect to each other. In lieu of segment 16, a short unique segment would be present between the TBR and PS inserts, such segment being provided by additional nucleotides in the polylinker, or by a third insert in between TBR and PS. In addition, a restriction enzyme site, which is not present in any of the inserts, is present at the end of the inserted region farthest from the SP6 promoter.

In use, the plasmid DNA would be prepared and digested with the restriction enzyme at the end of the insert region to linearize the plasmid. Full-length RNA would be transcribed from the linearized plasmid using purified SP6 polymerase. DNA would be removed with (RNase-free) DNase digestion, and the RNA purified by phenol/chloroform extraction and ethanol precipitation or Sephadex Column Chromatography. Under optimal conditions, up to 10 ug of RNA can be obtained from 1 ug of plasmid in a 50 ul reaction mixture.

The product of this reaction would be an RNA molecule with a duplex region formed by intramolecular hybridization of PS to the LBR region of TBR. TBR and PS would be connected by the single stranded RNA segment DNA oligomer (typically 6 or more nucleotides in length) complementary to this connecting segment would be provided after transcription. By hybridizing with DNA oligomer and digesting the DNA/RNA hybrid specifically with RNase H (see H. Donis-Keller, *Nucleic Acids Res.*, vol. 7, pp. 179-192 (1979)), specific cleavage of the loop connecting TBR to PS could be accomplished.

In effect, the manufacture of RNA constructs involves steps analogous to FIGS. 1A-1E with the DNA counterpart, but with the segment defined by Bam HI cleavage in the DNA counterpart being defined by transcription of the region between the SP6 promoter and the restriction enzyme cleavage site distal to the inserted region (for example, the Eco RI site when SP64 constructs are used, by Hind III when SP65 constructs are used). Forming the RNA/RNA hybrid segments could be performed simultaneously with forming the DNA oligomer/RNA hybrid (analogous to segment 16). Labeling could follow or precede such hybrids being formed and/or cleavage with RNAse H. Attachment and/or labeling could be performed using the techniques of E. Brown, et al., U.S. Ser. No. 729,700, now abandoned.

EXAMPLE 1

Figure 5A:
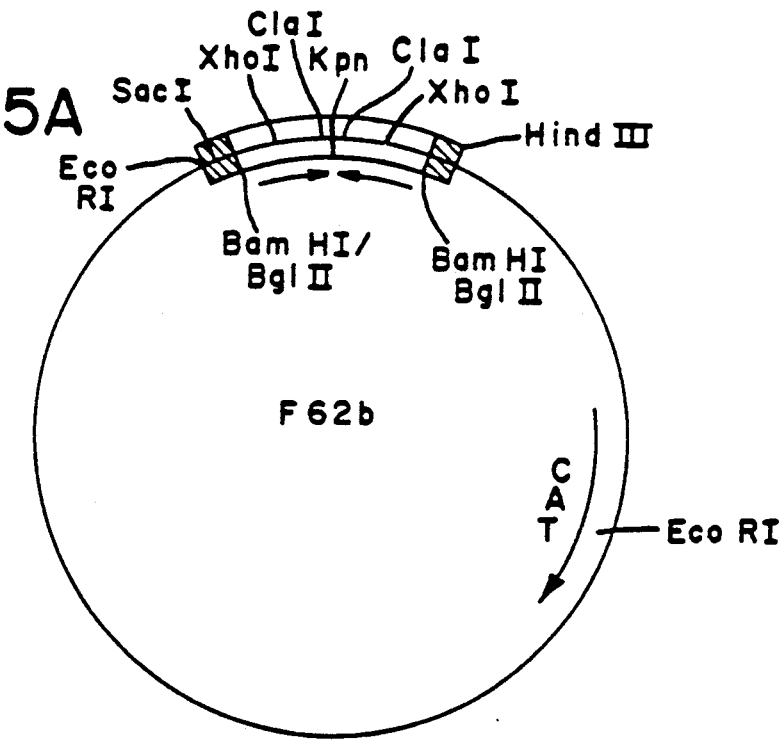
Figure 5B:
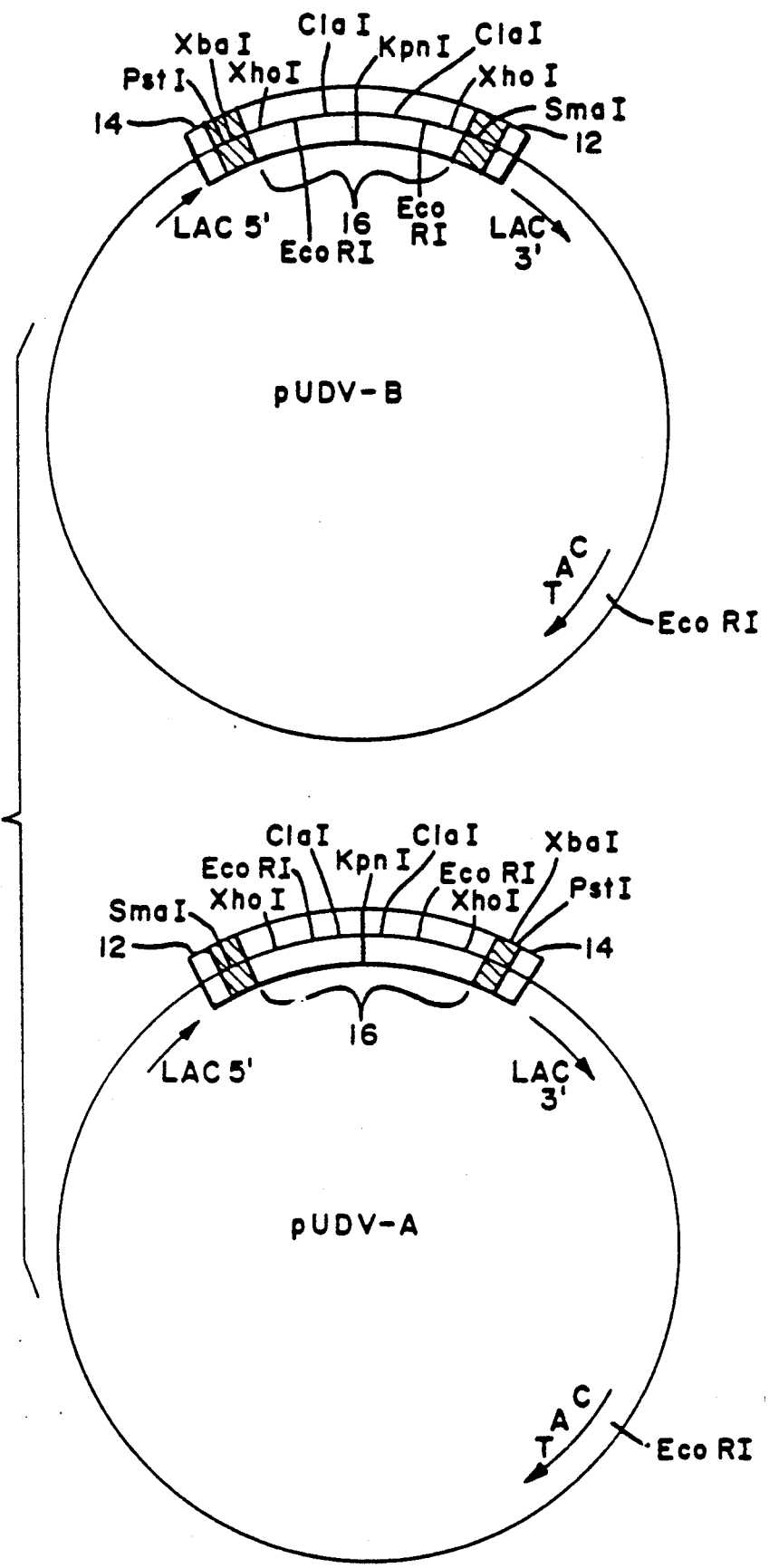

Preparation of Nucleic Acid Molecule Containing Target Binding Region For Albumin Gene And Pairing Segment This example describes the preparation of a replicable, continuous nucleic acid molecule in double-stranded form (i.e., with its complementary strand) containing a target binding region for 500 bases of a human albumin gene. The starting materials were *E. Coli* plasmids, each containing an M13 origin of replication, designated pMLC12 and pMLC13. These two plasmids were, in turn, prepared by partial Hind III digestion and Klenow end fill of the plasmids pSDL12 and pSDL13 (see FIG. 5 and accompanying description of A. Levinson et al., *J. Mol. & Appl. Gen.*, vol. 2, pp. 507-517 (1984).

A) Preparation of PmLC12/13Δ M7 (M13 ori plasmid with Mp7 polylinker)

pMLC12 and pMLC13 were digested with EcoRI to completion. The large fragment from pMLC12 (Fragment A) and the small fragment from pMLC13 (Fragment B) were combined, ligated and transformed into MC1061 (F−;hsdR, Δ ara-leu 7697, araD139, Δ lac X 74, galU, galK, rpsL (str$^r$) Casadaban Y. Cohen, *J. Mol. Biol.* vol 138 pp. 179-207. Chloramphenicol resistant colonies were picked and the correct plasmid (pMLC12/13Δ) was identified on the basis of loss of the BamHI cleavage site seen in both the original pMLC12 and pMLC13 plasmids.

pMLC12/13Δ was digested partially with EcoRI by use of limited amounts of EcoRI so that only one of the two EcoRI sites is digested in most molecules. The partially cut, linearized pMLC12/13Δ was isolated following gel electrophoresis. Mp7 DNA was digested with PvuII and a 383 bp fragment was isolated following gel electrophoresis. The PvuII fragment was digested with EcoRI to produce the 52 bp EcoRI fragment containing the Mp7 polylinker and two other PuvII/EcoRI fragments (about 123 bp and about 208 bp). The EcoRI digested PuvII fragment from Mp7 and the linearized, partially EcoRI digested pMLC12/13Δ were ligated transformed into MC1061 and chloramphenicol resistant cells were selected. Individual colonies were then grown and DNA was prepared. Plasmids which had correctly incorporated the EcoRI polylinker from Mp7 were identified by the aquisition of a BamHI site. The correct plasmid, termed pMLC12/13Δ M7, is shown in FIG. 4A.

B) Construction of Albumin inverted repeat in pMLC12 pMLC12 was digested to completion with HincII. The plasmid pAlbB6 which contains a portion of a human albumin cDNA clone (see Lawn et al., 1980) was digested to completion with PvuII and HincII. The fragment which we wish to clone is the 915 bp PuvII/HincII fragment. The pMLC12/HincII vector and pAlbB6/PuvII+HincII were ligated together and transformed into MC1061. Clones which had incorporated the correct albumin fragment were identified by colony hybridization (Grunstein and Hogness, 1976) using the alb 32mer (5′ACATCCTTTGCCTCAG-CATAGTTTTTGCAAAC3′) as a hybridization probe. Positive colonies were picked and grown up; and DNA from individual colonies was digested with HindIII+PstI to determine the orientation of the inserts. Two plasmids with the albumin fragment insert into the vector in opposite orientations (F31a and F31c) were selected for further steps. Plasmids F31a and F31c are shown in FIG. 4B.

F31a was digested to completion with EcoRI+BamHI and the two large fragments were isolated. F31c was digested to completion with EcoRI+BglII and the small (approximately 550 bp) fragment (between the RI and Bgl II sites) was gel isolated. The gel isolated fragments from F31a and F31c were ligated together and transformed into DH1 (ATCC #33849) a recA− bacterium. (Note: A recA− host was used at this point to reduce the possibility of deletion of one or both copies of the inverted repeat through a recA mediated mechanism. Subsequent experiments have shown that these inverted repeat clones are stable even in the absence of recA−mutation.) DNA was then prepared from individual chloramphenicol resistant colonies and digested separately with PstI, EcoRI plus HindIII, or BglII plus Bam HI to identify clones with the correct structure. One such clone F41a (shown in FIG. 4B) was used for further analysis.

Figure 4C:
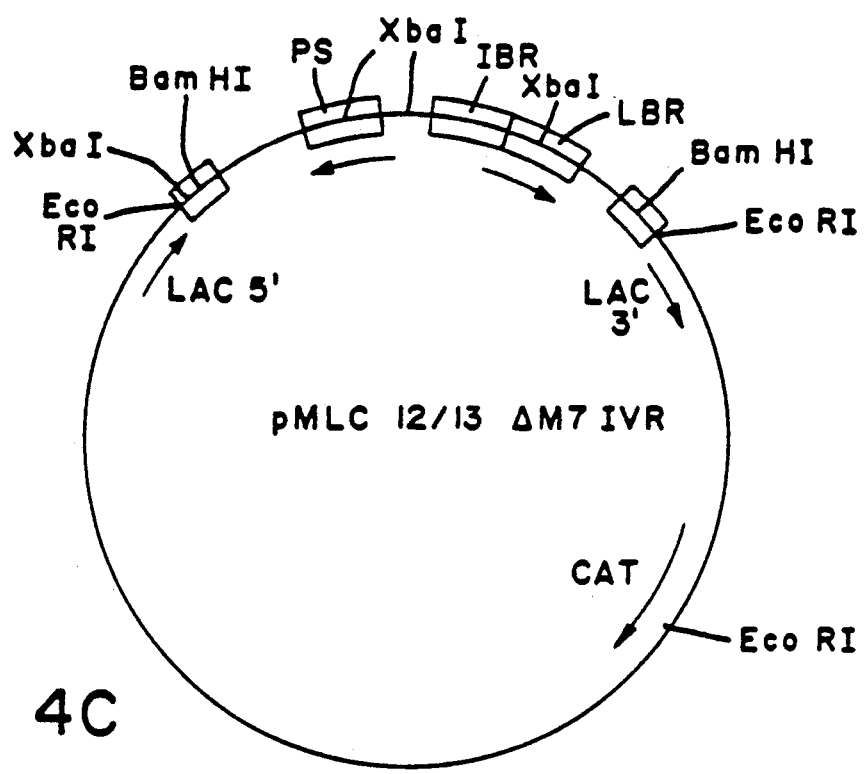

F41a was digested with EcoRI and HindIII and blunted with the klenow fragment of DNA Polymerase I. The approximately 1500 bp fragment was isolated following gel electrophoresis. pMLC 12/13Δ M7 was digested to completion with Acc I and blunted with the klenow fragment of DNA Polymerase I. The pMLC12/13Δ M7/AccI+klenow [fragment] and the gel-isolated fragment from F41a were joined by DNA ligase and transformed into MC1061. Plasmids which had incorporated the gel isolated fragment were identified by hybridization to the albumin 32 mer and were verified by digestion with PstI, BamHI, or XbaI. This plasmid, termed pMLC12/13ΔM71Vr, is shown in FIG. 4C.

For the next step, plasmid MpTL poly was used. This plasmid had been previously prepared by phosphorylating the lower oligonucleotide strand of:

After ligating, a dimer was isolated having the middle portion:

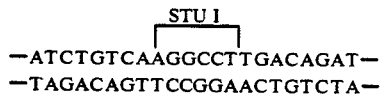

recognizable because of the Stu I site that had formed. The dimer was filled with Klenow fragment of DNA polymerase I so as to have the end portions:

with the underlined base having been filled in by Klenow. This duplex was now cloned into Mp8/Hinc II and a clone picked on the basis of acquisition of a Stu I site. After sequencing for confirmation, the resultant plasmid was MpTL poly.

pMLC12/13ΔM71VR was partially digested with XbaI (which cuts four times within the plasmid), blunted as above, and full length linearized plasmid DNA was isolated by gel electrophoresis. The plasmid MpTL poly was digested to completion with BamHI+HindIII and was blunted as above. The 80 bp blunted fragment was isolated by gel electrophoresis and ligated to the gel isolated, linearized, XbaI partially cut, blunted pMLC12/13ΔM71VR. The DNA was transformed into MC1061 and screened with the oligonucleotide which is complimentary to the TL polylinker. Positive colonies were picked and plasmid which had incorporated the TL polylinker at the correct XbaI site was identified by digestion with StuI+Bgl II. This plasmid, termed pMLC12/13Δ M71VRTL, is shown in FIG. 4D, and is analogous to FIG. 1C.

Figure 4D:
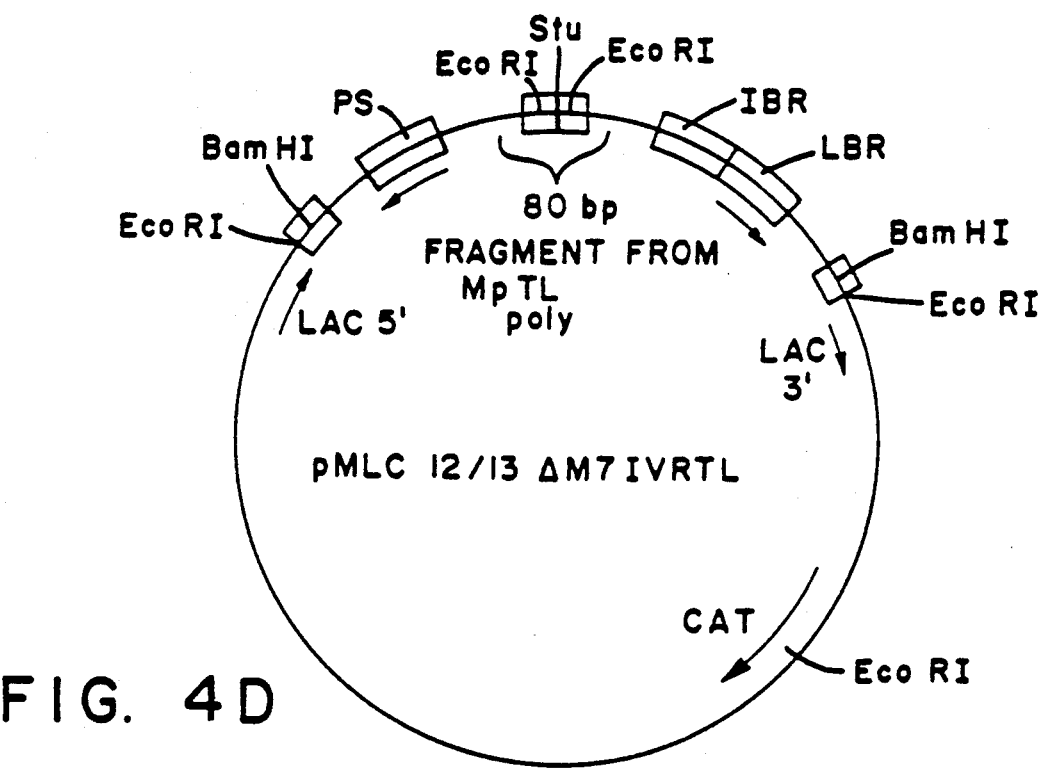

Two other constructions could be carried out as for the one shown in FIG. 4D, above, except that the TL polylinker plasmid would be replaced by:

a) a HincII/StuI fragment from the human erythropoietin cDNA (Jacobs et. al., Nature, 1985) which contains two HaeIII sites (which will digest in single-stranded DNA; the albumin cDNA has no HaeIII sites).

b) a BglII/blunted fragment from F62b (see description of FIG. 5A, below) which contains the polylinker with the XhoI, EcoRI, XbaI and ClaI sites.

These three clones then provide the possibility for alternative digestions to separate the signal strand from the probe strand.

C) Production of single-stranded DNA

Figure 4E:
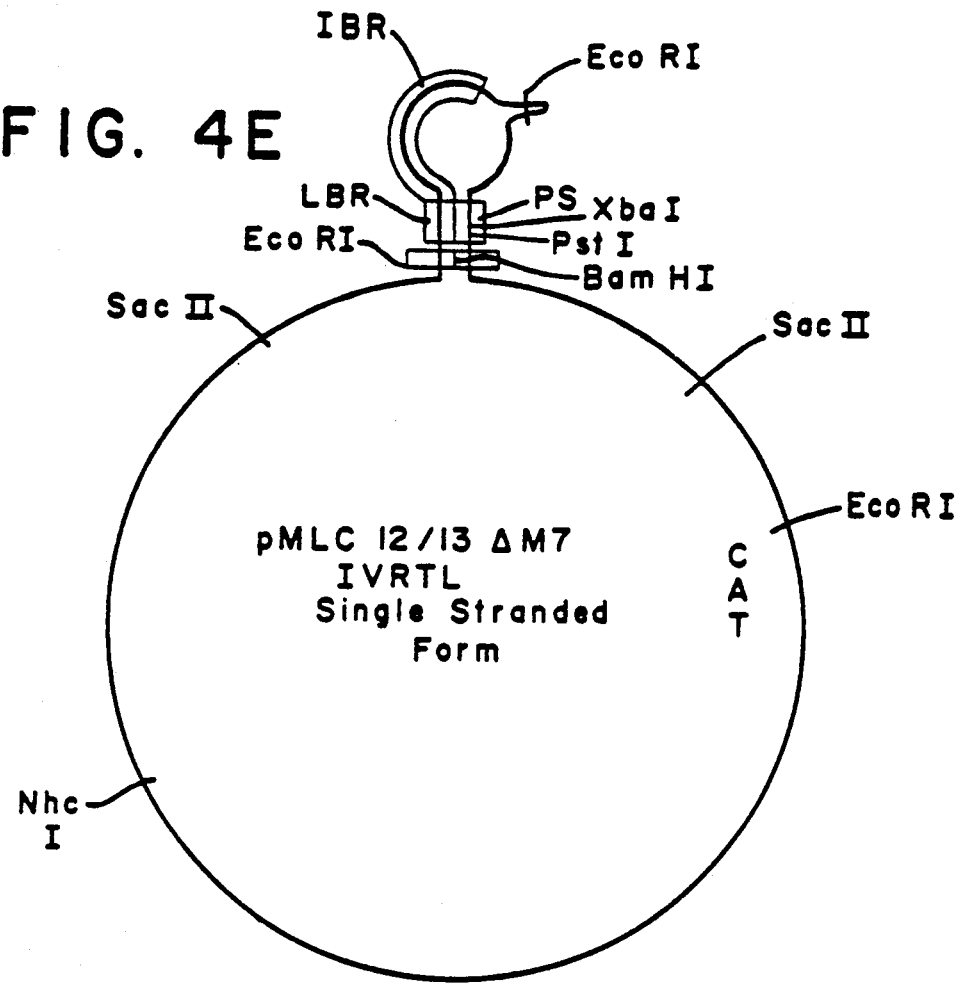

The plasmid pMLC12/13Δ M71VRTL (see FIG. 4D) was transformed into the strain XS127 (argE(am), thi-1, ΔlacproXIII/F'lacproAB, traD36, lacIq, lacZΔ M15/p3) or JM101 (ATCC #33876) which is used to produce single-stranded DNA from M13 ori plasmids. An overnight culture, (about $3 \times 10^9$ cells) was mixed with $5 \times 10^{10}$ wild type M13 phage, diluted to 100 ml in SOBM media and grown for 5 hours at 37° C. Single-stranded DNA was prepared from the culture supernatant using standard procedures. FIG. 4E shows diagrammatically the regions of single- and double-stranded DNA which should form in this nucleic acid molecule from its complementary strand.

Digestion of this DNA with BamHI, PstI, XbaI, and EcoRI, alone or in various combinations, produced the predicted fragments.

EXAMPLE 2

Preparation Of Reagent Complex From Replicable Nucleic Acid Molecule

Single-stranded DNA from pMLC12/13Δ M71VRTL (see FIG. 4E) was digested with BamHI and the resulting 3' recessed BamHI end was filled in with alpha $\alpha$ $^{32}$P-dATP and cold dCTP, dGTP, TTP. The reaction was incubated at 68° C. for 10 minutes to heat inactivate the klenow fragment of DNA Polymerase I and digested to completion with EcoRI. The resulting DNA was chromatographed twice over an hydroxylapatite (HAP) column in 0.12M phosphate buffer (pH 6.8) to isolate the partially double-stranded labeled molecule from the major portion of the vector. Following binding to the HAP column in 0.12M phosphate buffer and washing, partially double-stranded labeled construct was eluted from the HAP column with 0.3 M phosphate buffer and concentrated.

EXAMPLE 3

The isolated reagent complex (about 12 ng) of Example 2 was then incubated in a 10 ul volume of 20 mM Tris pH 8, 1M NaCl, 10 mM EDTA, at 65° C. for 60 minutes alone or with about 300 ng of single-stranded DNA from M13 clones G7c and G7e, which contain the albumin Hinc III/Pvu II 915 base pair fragment cloned into the Sma I site of the vector Mp8 in opposite orientations or no DNA. The labeled strand was completely displaced from the reagent complex in the presence of the competing strand (G7c) and was not displaced in the absence of competing strand (G7e; no DNA), as measured by gel electrophoresis and autoradiography.

EXAMPLE 4

Construction of Nucleic Acid Precursor

The double-stranded IV polylinker

```
AGATCTCGAGAATTCTAGATCGATGGTACC
TCTAGAGCTCTTAAGATCTAGCTACCATGG
``` was prepared by chemical synthesis and inserted into a modified pUC plasmid in both orientations (a and b). The plasmid pUC is described by Viera and Messing, Gene, vol. 19, pp. 259-268 (1982). The pUC plasmid was modified in several ways, the only one of which is relevant to present Example being the addition of an SfiI linker at a site in the plasmid other than the site at which the IV polylinker was subsequently added. The orientation (A) where the SfiI site was closest to the BglII site was digested with SfiI and Kpn I and the small fragment was isolated. The orientation (B) where the Sfi I site was closest to the Kpn I site was digested with Sfi I and Kpn I, and the large fragment was isolated. The gel isolated fragments were ligated and transformed into MC1061. The desired clone, containing two copies of the polylinker in opposite orientation with the KpnI site in the middle was identified by BglII digestion, end labelling with α $^{32}$P-dATP and the klenow fragment of DNA Polymerase I and gel electrophoresis before and after KpnI digestion. The resulting plasmid is termed F58a.

F58a was digested to completion with BglII. The plasmid pMLC12 was digested with Bam HI and treated with Calf Intestinal Alkaline Phosphatase to remove 5' phosphate groups. The two DNAs were ligated and transformed into MC1061 and chloramphenicol resistant colonies were selected. Plasmids which had correctly inserted the BglII fragment with the IV polylinker were identified by ability of ClaI, XhoI, and KpnI to linearize the plasmid. The correct clone is termed F62b (see FIG. 5A).

F62b was digested with SacI and HindIII and blunted using the klenow fragment of DNA Polymerase I. The small 89 bp fragment was isolated following gel electrophoresis. The vector pMLC12/13Δ M7 (see Example 1, part A and FIG. 4A) and the 89 bp fragment were ligated and transformed into MC1061. Chloramphenicol resistant colonies were grown up and DNA was prepared. Colonies containing the 89 bp fragment were identified by XhoI or KpnI digestion (which will linearize the plasmid) and the orientation of the insert was determined by PstI plus SacI digestion. The two orientations of the plasmid designated pUDV-A and pUDV-B, shown in FIG. 5B, were assigned as follows: Orientation A produced two 253 bp SacI/PstI fragments and thus the PstI site was nearest to the 5' end of the CAT gene. Orientation B produced SacI+PstI fragments of 183 and 323 bp and thus the PstI site was farthest from the 5' end of the CAT gene. The nucleotide sequences of the inserts in both orientations of pUDV are given in FIGS. 1B and 2B, for orientations B and A, respectively.

EXAMPLE 5

If 5' end ligation is for solid support attachment, the target sequence is cloned into the blunted PstI site of pUDV-A, prepared in Example 4. The fragment cloned should have the target binding region TBR including the complement to the signal strand (LBR). The orientation of the first cloning step can be easily determined using either PuvII or SacII (which cut in the vector) and an enzyme which digests the insert DNA. Mini prep DNA is then prepared and digested with SmaI. This provides a blunt end site in which to clone the signal strand fragment. The orientation of the signal strand fragment is determined similarly and an orientation is chosen which is opposite to that of the target strand.

If the 5' is for signal attachment, then the cloning into the same sites is used for the same fragments but the vector pUDV-B is used.

Example 6

A similar vector to that prepared in Example 5 could be prepared in which the IV polylinker is replaced by the TL polylinker, whose structure is that described above in connection with plasmid MpTL poly (having EcoRI sites near each end and a StuI site at the middle of the polylinker). This polylinker would serve the purpose of segment 16/16' in FIGS. 1A and 1B.

EXAMPLE 7

The plasmid pUDV-A (see Example 4 and FIG. 2B) was digested with the enzyme Pvu II and the 399 nt fragment containing the cloned polylinker sequence was gel isolated (Fragment A). Pvu II cuts at two sites outside of the polylinker, but within the lac region sites shown in FIG. 2B. The vector pUC 118, obtained from Dr. Jeffrey Viera, is similar to vector pUC 18 (which is available commercially from New England Biolabs), but contains the M13 origin sequence (nucleotides 5465 (HgiA1 site) - 5941 (Aha I site) of the standard M13 map) inserted at the Nde I site of puC 18. That vector pUC 118 was digested with PVU II and the 2840 nt fragment containing the plasmid origin of replication, the ampicillin resistance gene and the M13 origin of replication was isolated (fragment B). Fragments A and B were ligated together and transformed into competent bacteria. Colonies containing plasmids with single inserts in the orientation wherein superinfection produces a template that contains (in the clockwise 5' to 3' orientation) amp (including a Bgl I site), Col El ori, Pvu II, mp7, Sma I, hairpin, Xba I, Hinc II, Pst I, mp7, Pvu II, Bgl I, M13 IG were identified by restriction mapping and hybridization with a strand specific oligonucleotide (5'-CGTTGTAAAACGACGGCC-3'). The resulting plasmid was termed p61A and produces a template containing the sequence such as is shown in FIG. 1B.

Subcloning of lambda fragments

A map of the relevant region of the bacteriophage lambda genome is given by Sanger, et al in Sanger, et al., J. Mol. Biol 162:301-302 (1982). Of interest are restriction sites of the following types at the following positions.

| Site | Position |
| --- | --- |
| Pst I | 16236 |
| Hae III | 16322 |
| Xmn I | 16914 |
| Kpn I | 17058 |
| Hinc II | 17077 |
| Hae III | 17294 |
| Pst I | 17395 |

The Pst I fragment of lambda containing this region was isolated by digestion with Pst I and gel electrophoresis. The 86 nt Pst I - Hae III fragment from position 16236 to position 16322 (the A fragment) was subcloned by digesting the isolated Pst I fragment of lambda with Hae III, isolating the 86 nt fragment and blunting the Pst I end with the Klenow fragment of DNA polymerase I. This fragment was then cloned into the Hinc II site of bacteriophage mp7 and the correct clone (mp7lambdaA) identified by hybridization with a specific oligonucleotide and by DNA sequence analysis. Similarly, the 163 nt Xmn I - Hinc II fragment from position 16914 to position 17077 (the D fragment) was subcloned by digesting the lambda Pst I fragment with Xmn I and Hinc II and gel isolating the resulting 163 nt fragment. This fragment was then cloned into the Hinc II site of mp7 resulting in mp7lambdaD.

Cloning into p61A

The clone mp7lambdaA (or mp7lambdaD) was digested with Bam HI and the insert fragment was blunted with the Klenow fragment of DNA polymerase I. This fragment was then cloned into the Sma I site of p61A and the desired strand specific oligonucleotide #1091 (for A; 5'-CCGTTATCCACGATGGCCTC-3') or #1090 (for D;5'-CATCGCCCGGTACATGGCG-3') resulting in the clones pA6 and pD10, respectively. The entire Lambda Pst I fragment was then inserted into the Pst I site of pA6 or pD10 and oriented by digestion with Kpn I. A map of the clones containing the lambda Pst I fragment in the desired orientations together with a diagram of the expected template folding pattern in the single stranded form of these plasmids would show structures analogous to structures represented as FIGS. 3E (pA6lambda2c) and 3C 6pD101ambda1a) except that the 5' and 3' ends become the 3' and 5' ends, respectively.

Proposed Use

Clones pA6lambda2c and pD101ambda1a (which contains the 86 nt and 163 nt pairing segments, respectively, but also containing the 1159 nt target binding region) are grown up in E. coli, superinfected with M13 and the harvested DNA is digested with Bam HI (producing constructs analogous to FIGS. 3E and 3C, respectively). The 5' ends of such constructs are labeled by the procedures of Examples 11 and 12, below, with an oligonucleotide containing a biotin moiety (see U.S. Ser. No. 729,700 of Brown, et al. now abandoned). The 3' ends of such constructs are elongated by action of the enzyme terminal deoxynucleotidyl transferase (TdT) with the nucleoside triphosphate dCTP to form an immobilizable oligo-dC tail. The complex can now be cleaved with the restriction endonuclease Eco RI to cleave the hairpin sequence. For assays involving capture by an immobilizable or immobilized strand having a sequence complementary to all or a portion of lambda sequence A (16236-16322) or of lambda sequence D (16914 to 17077), as in U.S. Ser. No. 809,971 now abandoned of Dougherty, et al, filed Dec. 16, 1985, such modification of the 3' end and such cutting of the hairpin are optional. Furthermore, if a biotinylation or other labeling technique not requiring free ends is employed, the harvested DNA prior to BamHI cleavage can be used for assays employing displacement and capture of the displaced pairing segment.

EXAMPLE 8

The cloning vector p61a described in Example 7 was used in this Example. Sequences from the cDNA sequence for erythropoietin (EPO) were used in this Example for target binding region, pairing segment and analyte. The relevant cDNA region, clone pG61aEPO-3III, has the map shown by Jacobs, et al in *Nature*, vol. 313, pp. 806-810 (1985) including:

| Site    | Position                                                  |
|---------|-----------------------------------------------------------|
| Eco RI  | 1 (inserted 6 bases upstream from initiator methionine codon) |
| Kpn I   | 133                                                       |
| Pst I   | 188; 363                                                  |
| Hinc II | 335                                                       |
| Pvu II  | 365                                                       |

The 175 base pair Pst I fragment (188-363) was cloned into the Pst I site of p61a plasmid DNA. Clones containing the insert were identified by hybridization to a kinased oligonucleotide probe. Single stranded plasmid DNA was prepared from positive colonies after superinfection with an M13 helper phage. The orientation of the Pst I fragment in the vector was determined by binding this single stranded DNA to nitrocellulose filters and hybridizing it with kinased oligonucleotide probes of opposite orientations. Plasmid p61A-EP03 contains the Pst I fragment in the orientation with the Hinc II site closest to the 3' end of the insertion.

Double stranded plasmid DNA was isolated from p61A-EPO3 and digested with Sma I. The 365 base pair Eco RI-Pvu II fragment (1-365) from the human EPO cDNA clone was gel purified and the Eco RI site was filled in with the Klenow fragment of DNA Polymerase I. This fragment was then ligated into the Sma I site of p61A-EP03; plasmids containing inserts were identified by screening colonies with a kinased oligonucleotide probe specific for this second insert. The orientation of the second insert was determined by analyzing Kpn I digests of the resulting double stranded plasmid DNA. Those plasmids with the target binding region and pairing segments in an inverted orientation contain a Kpn fragment of 166 base pairs, while those in the direct orientation contain a Kpn fragment of 264 base pairs. p61A-EP03-II was identified as having the target strand inverted with respect to the signal strand and was isolated for preparation of displacement complexes.

Single stranded p61A-EP03-II DNA was prepared as described in Example 1, except that the overnight culture was superinfected with the M13 phage derivative, MK107 (see Example 9) diluted to 100 ml in minimal media containing 50 ug/ml ampicillin and grown overnight at 37° C. The DNA was digested with Bam HI and the 3' end (near the 175 nt pairing segment) labeled with 32P-dATP using the Klenow fragment of DNA Polymerase I. The DNA was then digested with Eco RI to create final displacement complexes, by analogy with FIG. 1F.

The 370 base pair Eco RI-Pvu II fragment described above was also cloned into the Acc I site of the M13 phage vector mp7 after both the Acc I site and the Eco RI site were filled in with Klenow. Phage containing EPO inserts, and the orientation of those inserts, were identified by hybridization with kinased oligonucleotide probes. Single stranded template DNA was prepared from positive phage of each orientation and digested with Bam HI. The 370 nucleotide inserts were gel purified and used as model analytes.

Three displacement reactions were set up using this complex and either no analyte, excess analyte of the wrong orientation, or excess analyte of the correct orientation. No displacement was observed in the absence of analyte or with analyte of the wrong orientation.

Displacement was observed with analyte of the proper orientation, although the reaction did not go to completion due to incomplete digestion of the complex with Eco RI; such complexes bind analyte but do not release the signal strand from the probe strand after displacement.

EXAMPLE 9-13

This example and the examples that follow are illustrations of the capture methodology of U.S. Ser. No. 809,971 of Dougherty, et al, filed Dec. 16, 1985, and correspond to certain of Examples 2-10 of that application. The starting clone was pMLC12/13deltaM-7IVRTL, whose preparation is described above in Example 1, and whose structure is shown in FIG. 4D (double-stranded form) and FIG. 4E (single-stranded form).

The construct p66b was constructed by gel-isolating the double-stranded PvuII fragment containing the sequence of interest from the starting clone and ligating it to the gel-isolated Pvu II backbone of the M13 origin plasmid pUC 119 (similar to commercially available plasmid PUC 19, but containing the same M13 origin sequence as does pUC118, and also obtained from Dr. Jeffrey Viera). Single-stranded forms were obtained as described in Example 1, except that the DNA was transformed into the E. coli host strain MV1193 obtained from Dr. Michael Volkert (JM101 del(srlR-recA) 306::Tn10). Superinfection was with bacteriophage M13KO7. The use of the different pUC backbone, different E. coli host strain and different superinfecting M13 phage resulted in improved yields of the same construct after Bam HI digestion.

Inverse reagent complexes used in Examples 12 and 13 resulted from labelling the 5' end of p66b with P32.

p66d was constructed as described for p66b, except that the PvuII fragment was inserted into the pUC119 vector in the opposite orientation. The single stranded form of p66d produced after superinfection contains a displacement complex which is the complement of the p66b strand. Thus, before cleavage in the IVRTL hairpin, displacement complexes made from p66b contain the pairing segment at the 5' end and the target binding region at the 3' end.

II. Model Analytes: Model analytes were constructed by gel purifying a 2 kb Hind III-Eco RI fragment from a plasmid, pA11A1b, which contains the entire cDNA sequence of human albumin. The HindIII site is the HindIII site in the 3' end of the albumin cDNA. The EcoRI site is present in adjacent vector sequences. The vector sequences present on the HindIII EcoRI fragment have no bearing on the following examples. The HindIII - EcoRI fragment was ligated into Hind III-EcoRI digested M13mp8 and M13mp11 to give mp8A11A1b and mp11.A11A1b, respectively. Single stranded DNA was purified from phage containing these constructs, and was partially digested with Hae III to linearize these model analytes. There are no HaeIII sites within the albumin cDNA sequence. mp8.A11A1b template DNA is complementary to the target binding region of p66b displacement complexes, and mp11.A11A1b (see FIG. 4 of U.S. Ser. No. 809,971 now abandoned), template DNA is complementary to the TBR of p66d displacement complexes.

III. Model Capturers: Several different model capturers were constructed to help define the best geometry for capturing nucleic acid constructs.

c1. mp18.A1bTaqPst and mp19.A1bTaqPst were constructed by gel purifying a 350 base pair Bgl II-Pst I fragment from a human albumin cDNA clone, digesting it with Taq I, and ligating the resulting 280 base pair fragment into Acc I-Pst I mp18 and mp19 vectors. mp19.A1bTaqPst is complementary to the pairing segment (PS') of the labeled strand of p66b. mp18.A1bTaqPst is complementary to the pairing segment in p66d.

c2. mp8.A1bBH was made by ligating the 500 base pair Bgl II-Hinc II fragment from albumin cDNA into the Sma I site of mp8. The insert in mp8.A1bBH is coextensive with and complementary to the pairing segment in the p66b displacement complex described above.

c3. mp7delta.A1bXba constructs 1+, 2+, 3-, and 4- were made by digesting mp19.A1bTaqPst Rf DNA with Xba I and end filling, gel purifying the resulting 300 base pair fragment, and ligating it to the 6800 base pair gel purified Pvu II vector backbone fragment of mp7. Two resulting phage isolates containing single stranded albumin DNA complementary to the labeled polynucleotides of p66b displacement complexes are labeled 1+ and 2+, while two phage isolates containing the albumin strand complementary to probe polynucleotide strands of p66b are labeled 3- and 4-. Constructs 1+ and 2+ differ from mp19.A1bTaqPst in that a portion of the lac gene and all polylinker cloning sequences are deleted from the mp7delta backbone, and in that the albumin insert is complementary to a more interior portion of the signal strand (see FIG. 4 of U.S. Ser. No. 809,971).

c4. Biotinylation of mp7deltaA1bXba1+ and mp7deltaA1bXba3- DNA using Vector Laboratories Photoprobe ™ Biotin.

The capturing strands mp7deltaALbXba1+ or mp7deltaA1bXba3- were biotinylated using the commercially obtained Photoprobe Biotin (Vector Laboratories) essentially as described by the manufacturer and repeated below.

Photoprobe ™ biotin (500 ug) was resuspended in 500 microliter water as recommended by the manufacturer and stored in the dark at -20° C. 10 micrograms of template DNA from the clone mp7 deltaA1bTaqXbal+ or mp7deltaA1bXba3- were ethanol precipitated and resuspended in 10 microliter H$_2$O. The DNA was mixed with 10 microliter Photoprobe biotin solution under a safelight, sealed in a glass microcapillary pipette and irradiated by a sunlamp (GE infrared lamp 2JOR40/1) for 20 or 30 minutes in separate reactions. The sample was kept in an ice-H$_2$O bath during the entire irradiation procedure. After irradiation, the sample was removed from the capillary, diluted with 100 microliters of 0.1M Tris-HCl, pH 8.0, extracted twice with 2-butanol and precipatated following addition of 1/10 volume 3M Na Acetate and 2 volumes of ethanol. The precipatated sample was resuspended in 10 microliters 0.1 mM EDTA, pH 8.0.

Successful reaction was monitored by taking an aliquot of the biotinylated DNA and hybridizing a 32-P labeled oligonucleotide (cALB 32-mer) complementary to a 32 base segment of the capture strand. One-half of the sample (control) was then electrophoresed directly on an agarose gel. The other half was mixed with 10 microliter of streptavidin latex beads supplied from Pandex Laboratories in 0.2M NaCl, 20 mM Tris-HCl, pH 8.0, 0.1% NP-40 for 10-20 minutes at room temperature. After the binding step, the beads were removed from the solution by centrifugation (2 minutes, Eppendorf centrifuge) washed once and the combined solution phases were electrophoresed in a parallel lane to the control sample. Following electrophoresis and autoradiography, the results indicated that nearly all the 32-P labeled oligonucleotide sample that was hybridized to the mp7deltaA1bXbal+ DNA was removed from the sample that was exposed to the streptavidin latex, indicating that the majority of template DNAs (capture strands) had at least one biotin group attached.

EXAMPLE 10

Labeling of p66b Xba I complex by ligation of a kinased oligonucleotide results in decreased non-specific capturing In this experiment, p66b Xba complex was labeled by ligating a kinased oligonucleotide to the 3' end of the molecule. 10 pm of a 15 base oligonucleotide with the sequence 5' CTAGAGGCCTCTGCA3' was labeled at the 5' end with 32P -gamma ATP and polynucleotide kinase (see Maniatis et al, Cloning Manual (Cold Spring Harbor Laboratory 1982)). The labeled oligonucleotide was purified away from unincorporated 32P -γ ATP by centrifuging the reaction twice at 6000 rpm for 30 minutes in a total volume of 500 ul of TE in a Centricon 10 filtration device from Amicon. The kinased oligonucleotide and 1 pm of Xba I cut p66b gel purified complex were precipitated together with ethanol, and resuspended in 14 ul of TE. 4 ul of 5× ligase buffer (Maniatis et al Manual) and 2 ul of DNA ligase were added and the reaction was incubated at 15° for 4 hours. The reaction was diluted to 50 ul with TE, heated to 42° C. for 10 minutes to melt any non-ligated oligonucleotides and electrophoresed on a 1% agarose gel. Following electrophoresis, the gel was stained with ethidium bromide and viewed with a uv light box. Approximately 66% of the complexes ligated to each other, so that only 0.33 pm of complex were available for ligation to the kinased oligonucleotide. The kinased complex was purified and had an estimated specific activity of about $10^6$ cpm per pm.

Displacement and capturing reactions were carried out by incubating with either 0.001 pm (1000 cpm) or 0.005 pm (5000 cpm) of displacement complex with varying amounts of analyte and 0.2 pm of capturer in a total of 20 ul of 0.3M NaCl and 0.1773 M Tris HCl, pH 8.0, for 45 minutes at 65° C. In the absence of analyte, no non-specific specific capturing was observed in reactions with 0.001 pm of complex and 0.02 pm of either mp7, mp19, mp7deltaA1bXba3— or mp19.A1bTaqPst. The addition of 0.01 pm of analyte to these reactions resulted in 100% displacement, and in no detectable capturing in reactions with mp7, mp19, or mp7deltaA1bXba3—, and in greater than 90% captured complexes with mp19.A1bTaqPst. In reactions with 0.005 pm of complex, in the absence of analyte no detectable capturing was observed with mp7deltaA1bXba3—, less than about 0.5% non-specific capturing was observed with mp7, mp19 and mp19.A1bTaqPst. Slightly more background was observed with mp19.A1bTaqPst than with mp7 and mp19. In the presence of 0.01 pm of analyte, less than 1% capturing was observed with mp7, mp19, or mp7delta.A1bXba3—, while greater than 90% capturing was observed mp19.A1bTaqPst.

These results indicate that lower background levels for non-specific capturing can be obtained using complexes which are labeled by ligation to a kinased oligonucleotide (or other techniques not causative of nicks). In addition, the absence of nonspecific capturing with mp7deltaA1bXba3-indicates that non-specific capturing at experimentally detectable levels is not an inherent property of the capturing concept.

EXAMPLE 11

Displacement and capturing with Bam HI p66b and mp7deltaA1bXba capturers

Single stranded p66b DNA was digested to completion with Bam HI, and the covalent complex was isolated by gel purification. A 32P-kinased oligonucleotide with the sequence 5'GATCCGCGGCGGTAC3' was ligated to the 3' end of the complex as described in Example [10] except that 2.4 pm of the complex and 10 pm of the oligonucleotide were used in the ligation reaction. The specific activity of the resulting complex was estimated at $8 \times 10^4$ cpm/pm.

Reactions were done by incubating either 0.01 pm (1000 cpm) or 0.03 pm (3000 cpm) in the presence or absence of 0.01 pm Hae III cut mp8.A11A1b analyte, with 0.1 pm of capture DNA in a final volume of 20 ul of hybridization buffer (0.3M NaCl, 0.1M Tris HC, pH8.0, and 10 mM EDTA) for 60 minutes at 65° C. Reactions were analyzed by gel electrophoresis (1% agarose gel) and autoradiography.

In the absence of analyte, no detectable background capturing was observed with any of the following capturers: mp7, mp19, mp7deltaA1bXbal+, mp7deltaA1bXba3— or mp7deltaA1bXba4—. The addition of 0.01 pm of analyte to reactions with 0.01 pm complex resulted in 100% displacement; no capturing was observed with the mp7deltaA11bXba4— capturer, and 100% capturing was observed with the mp7deltaA1bXbal+ capturer. The addition of 0.01 pm of analyte to reactions with 0.03 pm complex resulted in approximately 50% displacement and no capturing with mp7deltaA1bXba4— and complete capturing of the displaced complexes with mp7deltaA1bXbal+.

EXAMPLE 12

Comparison of displacement and capturing with covalent and non-covalent p66d complexes Covalent p66d displacement complexes were prepared and labeled at the 5' end by ligation of the kinased 16mer using the EF21 splint as described in Example 13. The specific activity of the resulting complexes was about $1 \times 10^6$ cpm/pm.

Non-covalent p66d complexes were produced by complete digestion of approximately 50 ug of single stranded templated DNA with Bam HI and Eco RI. Complete digestion was ascertained by the appearance of equimolar amounts of three bands, corresponding to vector backbone, target strand, and signal strand, after electrophoresis of a small aliquot of the digest on an alkaline gel. Non-covalent p66d complexes were labeled at the 5' end of the signal strand as described for covalent complexes, by EF21 splint ligation of a kinased 16mer, with a resultant specific activity of $3 \times 10^6$ cpm/pm.

The four reactions outlined in Table 3 were set up in a total volume of 50 ul of hybridization buffer and incubated for 60 minutes at 65° C. using HaeIII digested mp11.A11A1b DNA as analyte and biotinylated mp7deltaA1bXba3— capturere. 10 ul of each reaction were analyzed by gel electrophoresis and autoradiography, and the remaining 40 ul by binding to steptavidin agarose. 200 ul packed volume streptavidin agarose was used per reaction. Binding and washing was as described in Example 13 (below), except that, after binding, the pellet was rinsed 3 times for 30 minutes at room temperature and once for 60 minutes at 65° C. The final pellet and all supernatants were counted. Data showing the cpm bound to agarose after each rinse are given in Table 1. These results show that displacement and capturing are approximately equally effective for covalent and non-covalent complexes.

Gel analysis of the same reactions, as well as two reactions in which only displacement complex and capturer were included, demonstrated that 100% of the complexes were displaced by analyte, and when capturer was included, 100% capturing occurred. In the absence of analyte, no capturing was observed. In addition, since complexes which have hybridized both to capturer and analyte (i.e., captured covalent complexes or the second intermediate) migrate differently from capturers which have hybridized only to signal strand displaced from noncovalent complexes, one can distinguish capturing intermediates ("second intermediates") which contain capturer hybridized to analyte which in turn is hybridized to the target binding region of the displacement complex, from those non-covalent complexes which have resolved to contain only capturer and displaced signal strand. In this experiment, approximately 90% of the captured signal is present in the resolved form, despite the fact that capture DNA was present in excess over analyte and complex, and would be likely to form the intermediate structure before displacement.

TABLE 1

| REACTION | pm COMPLEX | pm ANALYTE | pm CAPTURER |
|---|---|---|---|
| 1 | 0.2 covalent | 0.2 | 0.8 |
| 2 | 0.2 noncovalent | 0.2 | 0.8 |
| 3 | 0.2 covalent | 0.2 | 0 |
| 4 | 0.2 noncovalent | 0.2 | 0 |

| | CPM BOUND TO SUPPORT | | | |
|---|---|---|---|---|
| | REACTION: | | | |
| | 1 | 2 | 3 | 4 |
| TOTAL: | 9821 | 26885 | 9318 | 30558 |
| RINSE 1: | 7932 | 24406 | 2403 | 5625 |
| RINSE 2: | 7383 | 22793 | 1267 | 1859 |
| RINSE 3: | 7055 | 20363 | 827 | 956 |
| RINSE 4: | 6186 | 19063 | 666 | 512 |
| FINAL | 5562 | 16718 | 304 | 299 |
| % BOUND: | 55.6% | 62.1% | 1.7% | 1.0% |

EXAMPLE 13

Large scale displacement and capture with trapping on streptavidin agarose

The Bam p66b displacement complex was labeled to a specific activity of about $10^6$ cpm/pm by ligating a 32P-kinased oligonucleotide to the 5' end of the complex with the use of a 21 base splint (EF21). 10 pm of the kinased 16mer (indicated below by the asterisk), 10 pm of splint, and 1 pm of p66b Bam (underlined below) were incubated together at 22° C. for 15 minutes in 10 ul of 1×ligase buffer; 1 ul of ligase was added and the reaction incubated for an additional 30 minutes. The three molecules form the structure diagrammed below.

```
*CGAAGCTTGGATCCGCGATCCGTCAGCTT...p66b
         GAACCTAGGCGCTAGGCAGCT    (SPLINT)
```

The four reactions outlined in Table 2 were set up in a total volume of 50 ul of hybridization buffer (see Example 14) and incubated for 30 minutes at 65° C. Hae III cut mpAllAlb and biotinylated mp7delta.AlbXba DNA were used as analyte and capturer, respectively. 25 ul of each reaction was then analyzed by gel electrophoresis and 25 ul by binding to streptavidin agarose as follows. 100 ul packed volume of streptavidin agarose was washed twice in 500 ul binding buffer in a 5 ml Sarstedt tube rotated end over end for 15 minutes, and pelleted by centrifugation. The 25 ul reaction aliquots were diluted to a total of 500 ul binding buffer, and incubated, rotating as above, for 15 minutes. The sample was transferred to an Eppendorf tube for centrifugation, the supernatant saved, and the pellet rewashed as above, once at room temperature for 15 minutes, then twice at 65° C. for 15 minutes, then for 60 minutes at room temperature and finally for 15 minutes at room temperature with TE. The final pellet and all supernatants were counted. Data showing the cpm bound to agarose after each rinse are given in Table 2. These results show that binding of complex to the support is dependent upon the presence of capturer and analyte, and on the amount of analyte present.

Gel analysis of the same reactions indicated that there is less than 0.05% non-specific capturing in these reactions. Specific capturing was more efficiently analyzed by gel separation, in that the presence of analyte resulted in capturing of approximately 80% and 20% of the complex in reactions 3 and 4, respectively.

It should be noted that this Example 13 and Example 14, below, provide labeling at the 5'-end, and thus adjacent to the target binding region rather than to the pairing segment. Such a geometry is described further in a copending application of Collins et al, U.S. Ser. No. 809,992, filed Dec. 16, 1985, now U.S. Pat. No. 4,752,566.

TABLE 2

| REACTION | pm COMPLEX | pm ANALYTE | pm CAPTURER |
|---|---|---|---|
| 1 | 0.10 | 0 | 0 |
| 2 | 0.10 | 0 | 0.16 |
| 3 | 0.10 | 0.05 | 0.16 |
| 4 | 0.10 | 0.01 | 0.16 |

| | CPM BOUND TO SUPPORT | | | |
|---|---|---|---|---|
| | REACTION: | | | |
| | 1 | 2 | 3 | 4 |
| TOTAL | 46435 | 42590 | 49423 | 41889 |
| RINSE 1: | 12915 | 10150 | 274308 | 15394 |
| RINSE 2: | 5254 | 3217 | 22982 | 10109 |
| RINSE 3: | 3911 | 2032 | 19978 | 7806 |
| RINSE 4: | 3500 | 1594 | 16261 | 6238 |
| RINSE 5: | 2203 | 1458 | 13780 | 5391 |
| RINSE 6: | 1482 | 1227 | 12351 | 4436 |
| FINAL: | 813 | 1044 | 10628 | 3658 |
| % BOUND: | 1.7 | 2.5 | 26.3 | 8.7 |

EXAMPLE 14

Prehybridization of complex and analyte, followed by capturing and trapping

Two additional reactions were done using the Bam p66b complex described in Example 13. In these reactions, 0.1 pm complex alone (reaction 1) or 0.1 pm complex and 0.05 pm Hae III cut mp8AllAlb analyte (reaction 2) were incubated in 50 ul of hybridization buffer for 30 minutes at 65° C. 0.16 pm of biotinylated mp7deltaAlbXbal+ was then added to both reactions, which were then divided and treated as in Example 13, except that all rinses were at room temperature with binding buffer. By gel analysis, less than 0.05% non-specific capturing, and approximately 40% specific capturing was observed. The results of analysis on streptavidin agarose (Table 3) indicate that capturing and trapping occur with approximately equal efficiencies whether capture DNA is added after (as in this Example 14) or is present during (as in Example 13) the analyte-dependent displacement reaction.

TABLE 3

| | CPM BOUND TO SUPPORT | |
|---|---|---|
| | REACTION | |
| | 1 | 2 |
| TOTAL: | 57860 | 55210 |
| RINSE 1: | 10364 | 18538 |
| RINSE 2: | 4360 | 14321 |
| RINSE 3: | 3046 | 11983 |
| RINSE 4: | 3035 | 9745 |
| RINSE 5: | 1781 | 8897 |
| FINAL: | 1124 | 7428 |
| % BOUND: | 1.9 | 13.5 |

EXAMPLE 15

Strand displacement, capturing and biotin displacement

In this experiment, the non-covalent p66d Bam HI/EcoRI cut displacement complex described in Example 12 was used. Hae III cut mpll.AllAlb DNA was used as the analyte. A capturer which has a single biotin at the 5' end was synthesized by primer extension of a 5' biotinylated M13 sequencing primer (biotinylated according to the method described in U.S. Ser. No. 729,700 of Brown, et al.) hybridized to mp19.AlbTaqPst as follows: 20 ug of mp19.AlbTaqPst template, and 20 pm of biotinylated primer in 100 ul of 50 mM NaCl, 10 mM Tris HCl, pH8.0, 10 mM MgCl₂ were boiled for 1' in a water bath and allowed to cool to room temperature for 30' in the bath. 3 ul of 5 mM dGTP, dCTP, dATP, dTTP and 2 ul of Klenow fragment Pol I were added, and the reaction incubated 30 minutes at room temperature. A second 1 ul aliquot of Klenow was added and the reaction incubated for 30 additional minutes. The DNA was then digested with Hind III for 2 hours at 37° C. to cut out the 300 base primer extended fragment which is complementary to the insert in mp19.AlbTaqPst. The DNA was denatured by adding 2 ul of 5 M NaOH and incubating it for 10' at 65° C. The primer extended fragment was purified after separation by electrophoresis on a 1% alkaline agarose gel with NA45 paper (Schleicher and Schuell). DNA yield was estimated by comparison of an aliquot of the capturer with standards on an ethidium stained gel.

Three reactions were set up as shown in Table 4. Reactions 1 and 2 were incubated for 60 minutes in 50 ul of hybridization buffer at 65° C. (reaction 3 was not incubated). 5 ul of reactions 1 and 2 were then removed for gel analysis. The rest of reactions 1 and 2, and reaction 3 were then bound as described in Example 8 to approximately 200 ul packed volume streptavidin agarose. In order to try and minimize sample agitation during the rinses, which may be responsible for a portion of the captured DNA separating from the support in earlier experiments, the samples were rinsed by adding 1 ml of binding buffer to the pellet in an eppendorf tube, inverting the tube five times, and centrifuging it for 3 minutes. Five rinses were done at room temperature, and a final rinse was done at 65° C. for 30 minutes with no shaking after the initial 5 inversions. All supernatents and the final pellet were counted. The results are shown in Table 4. As seen by these data, this gentler washing protocol, or the use of this new smaller and singly biotinylated capturer seems to promote more stable binding of the captured complex to the support. By cutting out and counting the appropriate bands from the gel analysis, it appears that approximately 36% of the captured complexes resolve to form capture-signal strand hybrids, while 64% are apparently present as analyte-complex-capturer intermediates under these reaction conditions.

TABLE 4

| REACTION | pm COMPLEX | pm ANALYTE | pm CAPTURER |
|---|---|---|---|
| 1 | 0.2 noncovalent | 0.2 | 0.5 |
| 2 | 0.2 noncovalent | 0 | 0.5 |
| 3 | 0.2 noncovalent | 0 | 0 |

| | CPM BOUND TO SUPPORT | | |
|---|---|---|---|
| | REACTION: | | |
| | 1 | 2 | 3 |
| TOTAL: | 25623 | 25524 | 29269 |
| RINSE 1: | 13618 | 2884 | 4802 |
| RINSE 2: | 12214 | 723 | 1927 |
| RINSE 3: | 11966 | 519 | 1511 |
| RINSE 4: | 11822 | 454 | 954 |
| RINSE 5: | 11693 | 391 | 845 |
| FINAL | 11174 | 233 | 687 |
| % BOUND: | 43.6% | 0.9% | 2.3% |

Biotin displacement of captured displaced strands

Reaction 1 to 3 as described above were used. Each sample was the final avidin-agarose pellet after the 30 minute, 60° C. wash described above. One ml BB containing 0.1% NP-40 (BB+) was added to each pellet at room temperature, shaken briefly by inversion and centrifuged to separate the phases (RT wash). One ml BB+ (at 65° C.) was then added and the samples were incubated for 5 minutes at 65° C. The samples were then centrifuged to separate the phases and washed twice with one ml BB+ at room temperature. The combined supernatant phases were then pooled (65° C./5'/-bio). The -biotin, 65° C. wash was repeated once more for sample 3 only. One ml of BB+ containing 1 mM biotin was then added to all samples and there were incubated for 5 minutes, centrifuged and washed as above (65° C./5'/+bio). The final pellet was resuspended in 3 ml BB+ and all samples were counted by Cherenkov counting. Table 5 presents the number of counts and the percentage (in parenthesis) of total counts recovered where applicable in each sample after the background (30 cpm) was subtracted.

TABLE 5

| TREATMENT | 1% | 2% | 3% |
|---|---|---|---|
| RT Wash | 42 | 2 | 57 |
| 65° C./5'/−bio | 182 | 16 | 103 |
| 65° C./5'/−bio | — | — | — |
| 65° C./5'/+bio | 7088 (84%) | 70 (54%) | 48 (6%) |
| Pellet | 1151 | 42 | 516 |
| Total | 8463 | 130 | 778 |

The signal to noise ratio before the biotin displacement can be defined as the ratio of counts in the reaction 1 pellet/reaction 2 pellet =48: (11174/233). The improvement brought about by the biotin displacement can be measured by the ratio of % counts released by biotin in reaction 1 over the percent counts released by biotin in either reaction 2 or 3. Thus by comparison with reaction 2 the improvement is 0.84/0.54=1.55 ×. For reaction 3 the improvement is 0.84/0.06=14 ×. The poor improvement seen in the reaction 2 sample is likely due to the fact that the reaction 2 capturer contains a small amount of M13 polylinker sequence which does result in some capturing by the biotnylated capturer in the absence of analyte. This capturing, though small, would lead to counts released by biotin. The reaction 3 sample (complex only) represents the type of background most likely to be found in an actual displacement measurement and therefore gives a better representation of the background improvement expected.

We claim:

1. A process for preparing a reagent complex for determining a target nucleotide sequence in the nucleic acid of a biological sample, which process comprises the steps:
   (a) producing by replication a continuous nucleic acid molecule predominantly in single-stranded form having:
      (i) a target binding region substantially complementary to the target nucleotide sequence, and
      (ii) a signal strand pairing segment bound by complementary base pairing to a portion of the target binding region; a second portion of the target binding region being single-stranded, and the target binding region and signal strand pairing segment being covalently linked by a phosphate-sugar backbone;
   (b) forming a first terminus adjacent to the signal strand pairing segment and a second terminus adjacent to the target binding region, with a nucleic acid strand including the target binding region and signal strand pairing segment extending from the first terminus to the second terminus; and
   (c) attaching a detectable tag to the nucleic acid strand having the target binding region, the signal strand pairing segment, the first terminus and the second terminus.

2. The process of claim 1 wherein the detectable tag is attached to a terminus adjacent to the signal strand pairing segment.

3. The process of claim 2 further comprising the step:
   (d) cleaving the phosphate-sugar backbone covalent linkage of the signal strand pairing segment to the target binding region, while retaining the complementary base pair binding between the signal strand pairing segment and a portion of the target binding region.

4. The process of claim 3 further comprising the step:
   (e) attaching an end of the nucleic acid molecule adjacent to the target binding region to a solid support.

5. The process of claim 4 wherein the attaching step (e) precedes the cleaving step (d) and the end attached is distal from the signal strand pairing segment.

6. The process of claim 4 wherein the attaching step (e) follows the cleaving step (d) and the end attached is created by the cleaving step (d).

7. The process of claim 2 further comprising the step:
   (d) attaching a moiety to the nucleic acid molecule at a terminus adjacent to the target binding region, the moiety being immobilizable by an affinity reagent.

8. The process of claim 2 wherein the first terminus and second terminus created in forming step (b) are a 3' end and a 5' end, and the attaching step (c) comprises selectively attaching the detectable tag to the first terminus.

9. The process of claim 8 wherein the first terminus is a 3' end and the attaching step (c) comprising elongating the 3' end with detectable nucleotides.

10. The process of claim 8 wherein the second terminus is a 5' end and the process further comprises attaching the 5' end to a solid support.

11. The process of claim 8 wherein the second terminus is a 5' end and the process further comprises attaching the 5' end to a moiety which is immobilizable by an affinity reagent.

12. The process of claim 1 wherein the detectable tag is attached to a terminus adjacent to the target binding region.

* * * * *